US010406191B2

(12) United States Patent
Li et al.

(10) Patent No.: US 10,406,191 B2
(45) Date of Patent: Sep. 10, 2019

(54) COMPOUNDS, EXTRACTS AND METHODS FROM CHINESE MEDICINAL HERB SOPHORA FLAVESCENS THAT INHIBIT AIRWAY CONTRACTION

(71) Applicants: Xiu-Min Li, Mamaroneck, NY (US); Hugh A. Sampson, NY, NY (US); Nan Yang, Flushing, NY (US); Kamal Srivastava, NY, NY (US); Charles Emala, NY, NY (US)

(72) Inventors: Xiu-Min Li, Mamaroneck, NY (US); Hugh A. Sampson, NY, NY (US); Nan Yang, Flushing, NY (US); Kamal Srivastava, NY, NY (US); Charles Emala, NY, NY (US)

(73) Assignee: Xui-Min Li, Mamaroneck, NY (US)

( * ) Notice: Subject to any disclaimer, the term of this patent is extended or adjusted under 35 U.S.C. 154(b) by 0 days.

(21) Appl. No.: 14/762,416

(22) PCT Filed: Jan. 21, 2014

(86) PCT No.: PCT/US2014/012306
§ 371 (c)(1),
(2) Date: Jul. 21, 2015

(87) PCT Pub. No.: WO2014/113784
PCT Pub. Date: Jul. 24, 2014

(65) Prior Publication Data
US 2015/0359834 A1     Dec. 17, 2015

Related U.S. Application Data

(60) Provisional application No. 61/754,831, filed on Jan. 21, 2013.

(51) Int. Cl.
| A61K 36/489 | (2006.01) |
| A61K 31/4375 | (2006.01) |
| A61K 31/7048 | (2006.01) |
| A61K 31/352 | (2006.01) |
| A61K 31/439 | (2006.01) |

(52) U.S. Cl.
CPC .......... *A61K 36/489* (2013.01); *A61K 31/352* (2013.01); *A61K 31/439* (2013.01); *A61K 31/4375* (2013.01); *A61K 31/7048* (2013.01)

(58) Field of Classification Search
None
See application file for complete search history.

(56) References Cited

U.S. PATENT DOCUMENTS

2005/0226943 A1* 10/2005 Yan ...................... A61K 31/353
424/725

FOREIGN PATENT DOCUMENTS

| KR | 20100126254 A | * 12/2010 | |
| WO | WO-2006046814 A1 | * 5/2006 | ........... A61K 36/489 |
| WO | WO 2011/071296 A2 | 6/2011 | |

OTHER PUBLICATIONS

Hoang et al. Phytother. Res. 21, 554-557 (2007).*
Craker et al. Herbs, Spices, and Medicinal Plants: Recent Advances in Botany, Horticulture, and Pharmacology (Herbs, Spices, and Medicinal Plants). vol. 1. p. 4. (Year: 1991).*
Dharmananda, S. "Sophora". Internet Archive: Sep. 7, 2001 [Retrieved from the Internet on: Dec. 3, 2017]. Retrieved from: <URL: https://web.archive.org/web/20010907204550/http://www.itmonline.org/arts/sophora.htm>. (Year: 2001).*
Sophora. From "The Plant List". Internet archive date: Dec. 1, 2012 [Retrieved from the Internet on: Dec. 3, 2017]. Retrieved from: <URL:https://web.archive.org/web/20121201080243/http://www.theplantlist.org/browse/A/Leguminosae/Sophora/>. (Year: 2012).*
Zoellner, EW., "Hypothalamic-pituitary-adrenal axis suppresion in asthmatic children on inhaled corticosteroids (Part 2)—the risk as determined by gold standard adrenal function tests: A systematic review", Pediatr Allergy Immunol, (2007), 18: 469-474.
Liang, B. et al., "Inhibitory Effect of Ku-Shen Sub-fractions on Murine Airway Smooth Muscle Contraction", J Allergy Clin Immunol, (Feb. 2010), 785, 1 page.
Lipworth, B.J. et al., "Systemic Adverse Effects of Inhaled Corticosteroid Therapy", Arch Intern Med, (May 10, 1999), vol. 159, 15 pages.
Salpeter, S.R. et al., "Meta-Analysis: Respiratory Tolerance to Regular Beta2-Agonist Use in Patients with Asthma", Ann Intern Med, (2004), 140, 802-813.
Kao, S.-T., et al., "Effects of xiao-qing-long-tang (XQLT) on bronchoconstriction and airway eosinophil infiltration in ovalbumin-sensitized guinea pigs: in vivo and in vitro studies", Allergy, (2001), vol. 56, 1164-1171.
Zhou, H. et al., "Anti-inflammatory and antiproliferative activities of trifolirhizin, a flavanoid from Sophora flavescens roots", J Agric Food Chem (Jun. 10, 2009), 57(11): 4580-4585.
Zhang, T. et al., "Pharmacology and Immunological Mechanisms of an Herbal Medicine, ASHMI on Allergic Asthma", Phytother Res., (Jul. 2010), 24(7): 1047-1055.
Wen, M. et al., "Efficacy and tolerability of antiasthma herbal medicine intervention in adults patients with moderate-severe allergic asthma", J Allergy Clin Immunol, (Sep. 2005), 8 pages.
Roland, N.J. et al., "The Local Side Effects on INhaled Corticosteroids: Current Understanding and Review of the Literature", CHEST, (Jul. 2004), 126(1): 213-219.
Noonan, M. et al., "Long-term safety of Mometasone Furoate administered via a dry powder inhaler in children: Results of an open-label study comparing Mometasone Furoate with Beclomethasone Dipropionate in children with persistent asthma", BMC Pediatrics, (Jul. 13, 2009), 9:43, 7 pages.

(Continued)

Primary Examiner — Amy L Clark
(74) Attorney, Agent, or Firm — Scully, Scott, Murphy & Presser, P.C.

(57) ABSTRACT

The present invention relates to extracts of *Sophora Flavescens*, and compounds isolated therefrom for use in modulating airway smooth muscle contractility. Methods of creating enriched extracts of *Sophora Flavescens* are disclosed, as are specific compounds isolated therefrom. Methods for the treatment of disorders involving airway smooth muscle, such as asthma, using the compounds and extracts described herein are also disclosed.

16 Claims, 18 Drawing Sheets

(56) References Cited

OTHER PUBLICATIONS

Figure 1A:
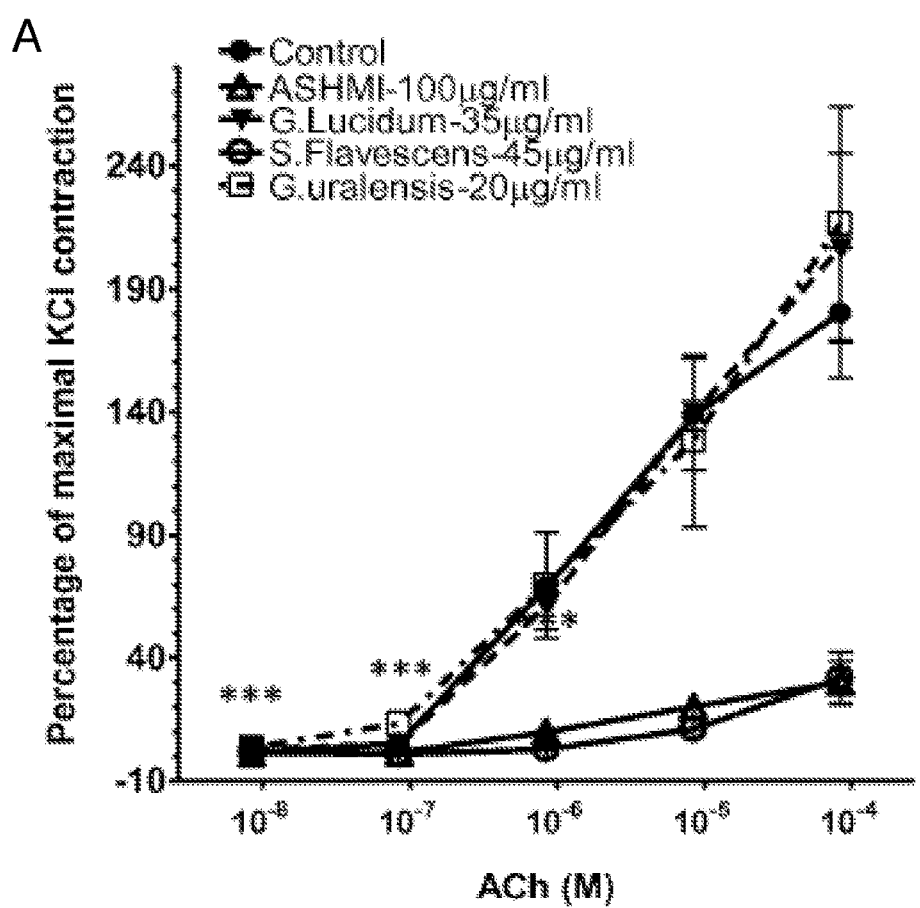
Figure 1B:
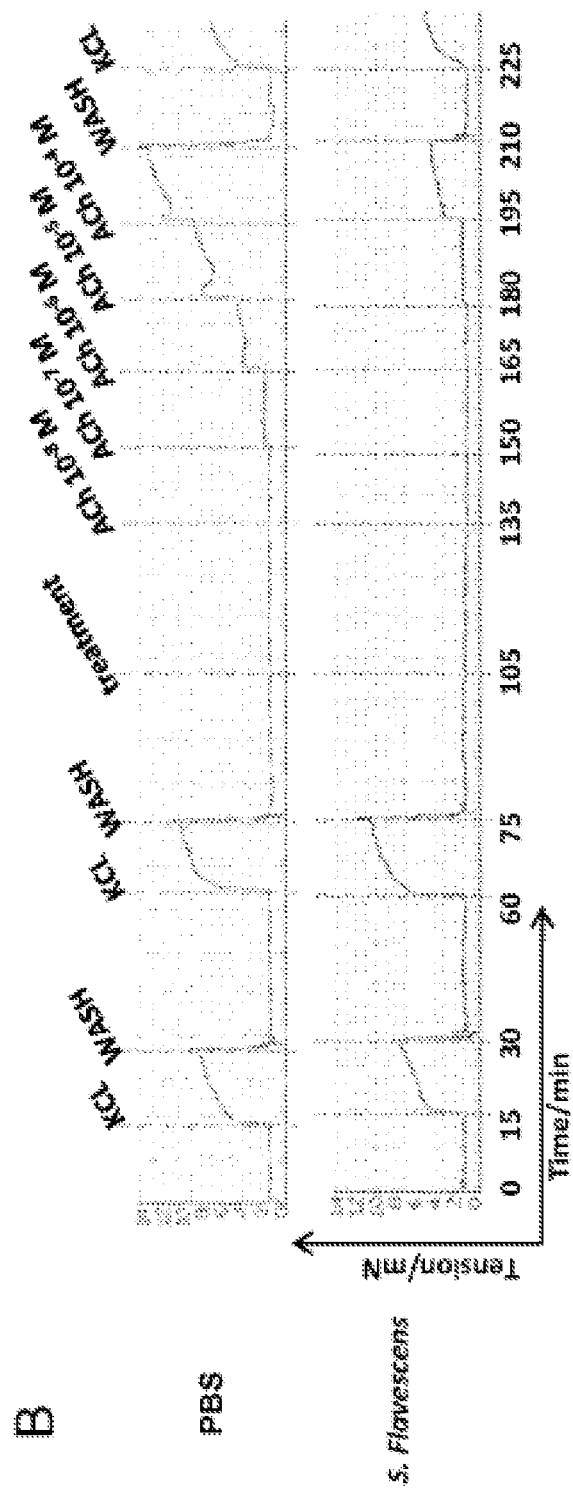

McGraw, D.W. et al., "Antithetic regulation by β-adrenergic receptors of Gq receptor signaling via phospholipase C underlies the airway β-agonist paradox", J. Clin. Invest., (2003), 112:619-626.

Li, X. et al., "The Chinese herbal medicine formula MSSM-002 suppresses allergic airway hyperreactivity and modulates TH1/TH2 responses in a murine model of allergic asthma", J Allergy Clin Immunol, (Oct. 2000), 106(4):660-668.

Li, X. et al., "Efficacy and mechanisms of action of traditional Chinese medicines for treating asthma and allergy", J Allergy Clin Immunol, (Feb. 2009), 123(2): 297-308.

Li, X. et al., "Complementary and alternative medicine in pediatric allergic disorders", Curr Opin Allergy Clin Immunol, (Apr. 2009), 9(2): 161-167.

Lemanske, R.F. et al., "A review of the current guidelines for allergic rhinitis and asthma", J Allergy Clin Immunol, (Feb. 1998), vol. 101, No. 2, Part 2, 5 pages.

Kelly-Pieper, K. et al., "Safety and Tolerability of an Antiasthma Herbal Formula (ASHMItm) in Adult Subjects with Asthma: A Randomized, Double-Blinded, Placebo-Controlled, Dose-Escalation Phase I Study", The Journal of Alternative and Complementary Medicine, (2009), vol. 15, No. 7, pp. 735-743.

Kawai, M. et al., "Flavonoids and Related Compounds as Anti-Allergic Substances", Allergology International, (2007), 56:113-123.

Hyun, S.K. et al., "Inhibitory Effects of Kurarinol, Kuraridinol, and Trifolirhizin from Sophora flavescens on Tyrosinase and Melanin Synthesis", Biol. Pharm. Bull. (2008), 31(1) 154-158.

Holgate, S.T. et al., "Roles of cysteinyl leukotrines in airway inflammation, smooth muscle function, and remodeling", J Allergy Clin Immunol, (Jan. 2003), 11(1): s18-S36.

Cordina, M. et al., "Anxiety and the management of asthma in an adult outpatient population", Ther Adv Respir Dis, (2009), 3(5) 227-233.

Busse, P.J. et al., "The traditional Chinese herbal formula ASHMI inhibits allergic lung inflammation in antigen-sensitized and antigen-challenged aged mice", Ann Allergy Asthma Immunol, (Mar. 2010), 104(3): 236-246.

Braman, S.S., "The Global Burden of Asthma", Chest, (2006), 130:4S-12S.

Billington, C.K. et al., "Signaling and regulation of G protein-coupled receptors in airway smooth muscle", Respiratory Research, (2003), vol. 4, No. 1, 23 pages.

Barrios, R.J. et al., "Asthma Pathology and Pathophysiology", Arch Pathol Lab Med, (Apr. 2006), vol. 130, pp. 447-451.

Akinbami, L.J. et al., "Status of Childhood Asthma in the United States, 1980-2007", Pediatrics, (Mar. 2009), vol. 123, Supplement 3, pp. S131-S145.

Abdel-Kader, M.S. et al., "Preliminary Pharmacological Study of the Pterocarpans Macckian and Trifolirhizin Isolated From the Roots of Ononis Vaginalis", Pak. J. Pharm. Sci., (Apr. 2010), vol. 23, No. 2, pp. 182-187.

Hoang, B.X. et al., "New Approach in Asthma Treatment using Excitatory Modulator", Phytotherapy Research, (2007), 21, 554-557.

Ye, G. et al., "LC-MS characterization of efficacy substances in serum of experimental animals treated with Sophora flavescens extracts", Biomed. Chromatogr., (2007), 21: 655-660.

Bhalla, R.K. et al., "The inflammation produced by corticosteroid inhalers in the pharynx in asthmatics", Clinical Otolaryngology, (2008), 33, 581-586.

Fukushima, C. et al., "Oral candidiasis associated with inhaled corticosteroid use: comparison of fluticasone and beclomethasone", Annals of Allergy, Asthma, & Immunology, (Jun. 2003), vol. 90, pp. 646-651.

"The Beta-agonist controversy revisited", The Lancet, (Jan. 17, 2004), vol. 363, pp. 183-184.

International Search Report dated May 29, 2014 issued in corresponding International Patent Application No. PCT/US2014/012306.

Jin, J.H. et al., "Anti-inflammatory and anti-arthritic activity of total flavonoids of the roots of Sophora flavescens", Journal of Ethnopharmacology, (2010), 127, 589-595.

Liu, G. et al., "Characterization of alkaloids in Sophora flavescens Ait. by high-performance liquid chromatography-electrospray ionization tandem mass spectrometry", Journal of Pharmaceutical and Biomedical Analysis, (2011), 54, 1065-1072.

Toogood, J.H. et al., "Effect of High-dose Inhaled Budesonide on Calcium and Phosphate Metabolism and the Risk of Osteoperosle", Am Rev Respir Dis, (1988), 138:57-61.

Wang, J. J. et al., "Use of Inhaled and Oral Corticosteroids and the Long-term Risk of Cataract", Ophthalmology, (Apr. 2009), vol. 116, No. 4, pp. 652-657.

* cited by examiner

A
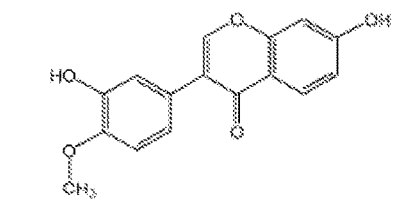
3',7-dihydroxy-4'-methoxy-isoflavone
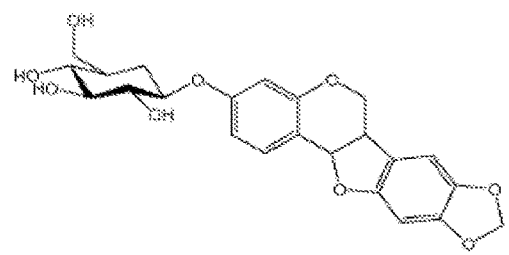
trifolirhizin
B
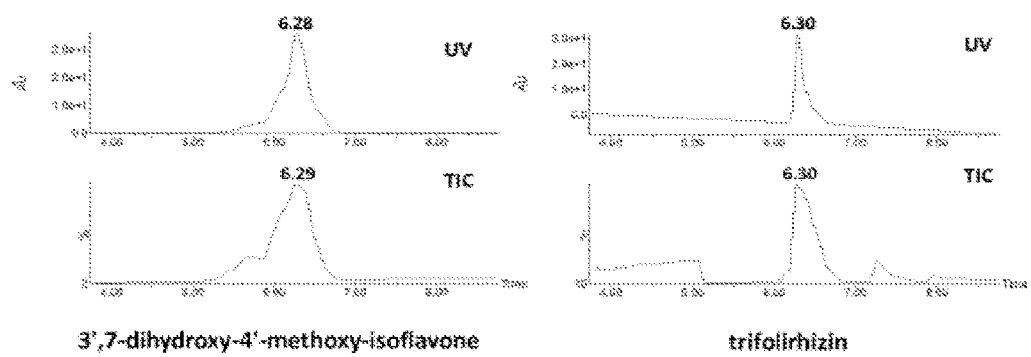
3',7-dihydroxy-4'-methoxy-isoflavone            trifolirhizin
C
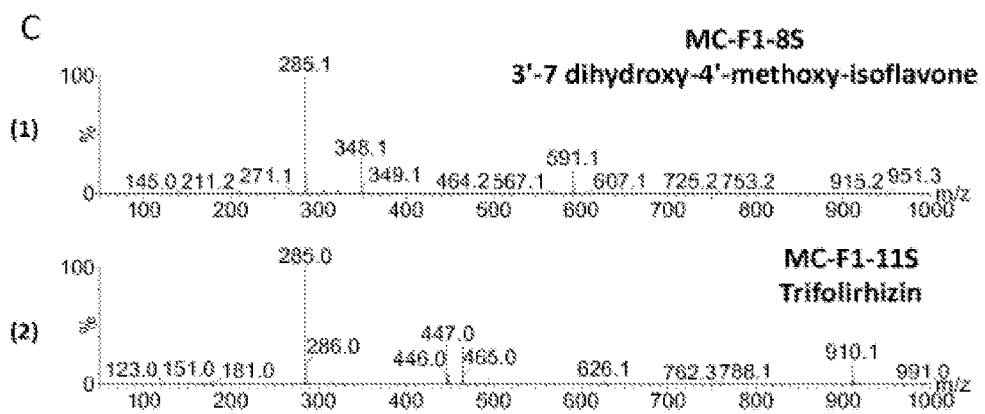
FIG. 5A - 5C Table 1

| | NMR spectra data of Trifolirhizin | | | NMR spectra data of MC-F1-11S | |
|---|---|---|---|---|---|
| No.C | $^{13}$C NMR | $^{1}$H NMR | No. C | $^{13}$C NMR | $^{1}$H NMR |
| 1 | 131.87 | 7.36 (d, J=8.8Hz) | 1 | 132.74 | 7.36 (d, J=8.6Hz) |
| 2 | 110.36 | 6.71 (dd, J=2.4, 8.8Hz) | 2 | 111.23 | 6.69 (dd, J=2.4, 8.6Hz) |
| 3 | 158.45 | | 3 | 159.31 | |
| 4 | 104.00 | 6.55 (d, J=2.4Hz) | 4 | 104.86 | 6.55 (d, J=2.4Hz) |
| 4a | 156.17 | | 4a | 157.04 | |
| 6 | 65.83 | 4.28 (dd, J=4.0, 10.4Hz); 3.68 (m) | 6 | 66.70 | 4.27 (dd, J=6.54Hz); 3.64 (m) |
| 6a | 40.13 | 3.45 (m) | 6a | 49.46 | overlap |
| 6b | 118.23 | | 6b | 119.09 | |
| 7 | 105.35 | 6.98 (s) | 7 | 106.22 | 6.99 (s) |
| 8 | 141.12 | | 8 | 142.00 | |
| 9 | 147.47 | | 9 | 148.33 | |
| 10 | 93.26 | 6.52 (s) | 10 | 94.13 | 6.53 (s) |
| 10a | 153.63 | | 10a | 154.49 | |
| 11a | 77.63 | 5.57 (d, J=7.2Hz) | 11a | 78.50 | 5.57 (d, J=6.89Hz) |
| 11b | 114.14 | | 11b | 115.01 | |
| 12 | 101.03 | | 12 | 101.90 | |
| | NMR spectra data of Trifolirhizin | | | NMR spectra data of MC-F1-11S | |
| No.C | $^{13}$C NMR | $^{1}$H NMR | No. C | $^{13}$C NMR | $^{1}$H NMR |
| 1' | 100.26 | 5.94 (d, J=0.8, 15.6Hz) | 1' | 101.13 | 5.94 (d, J=0.8, 11.0Hz) |
| 2' | 73.15 | 4.84 (d, J=7.6Hz) | 2' | 74.01 | 4.84 (d, J=5.81Hz) |
| 3' | 76.50 | overlap | 3' | 77.90 | overlap |
| 4' | 69.63 | overlap | 4' | 70.50 | overlap |
| 5' | 77.04 | overlap | 5' | 77.90 | overlap |
| 6' | 60.63 | overlap | 6' | 61.50 | overlap |

FIG. 16

Table 2

| | NMR spectra data of 3',7-Dihydroxy-4'-methoxy-isoflavone (calycosin) (CD3OD) | | NMR spectra data of MC-F1-8S (CHLOROFORM-D) | |
|---|---|---|---|---|
| No.C | $^1$HNMR | No.C | $^1$HNMR | |
| 2 | 8.11 (1H, s) | 2 | 7.91 (1H, s) | |
| 5 | 8.03 (1H, d, J=8.8Hz) | 5 | 8.19 (1H, d, J=8.58Hz) | |
| 6 | 6.92 (1H, dd, J=8.8, 2.3Hz) | 6 | 6.91 (1H, d, J=8.2Hz) | |
| 8 | 6.83 (1H, d, J=2.3Hz) | 8 | 6.86 (1H, d, J=2.0Hz) | |
| 2' | 7.03 (1H, d, J=1.2Hz) | 2' | 7.11 (1H, d, J=1.71Hz) | |
| 5' | 6.95 (1H, overlapped) | 5' | 6.91 (1H, d, J=6.5Hz) | |
| 6' | 6.95 (1H, d-like, J=1.2Hz) | 6' | 7.12 (1H, d, J=6.6Hz) | |
| OCH3-4' | 3.87 (3H, s) | 11 | 3.90 (3H, s) | |
| OH-3' | n.d. | OH-3' | 8.76 (1H, s) | |
| OH-7 | n.d. | OH-7 | 11.86 (1H, s) | |

FIG. 17

Table 3.1

| Fraction # | Properties |
|---|---|
| 1 | Dichloromethane soluble at neutral pH |
| 2 | Ethyl acetate soluble at neutral pH |
| 3 | Dichloromethane soluble at basic pH |
| 4 | Ethyl acetate soluble at basic pH |
| 5 | Dichloromethane soluble at acid pH |
| 6 | Ethyl acetate soluble at acid pH |
| 7 | Methanol soluble |
| 8 | Residue |

FIG. 18

COMPOUNDS, EXTRACTS AND METHODS FROM CHINESE MEDICINAL HERB SOPHORA FLAVESCENS THAT INHIBIT AIRWAY CONTRACTION

CROSS REFERENCE TO RELATED APPLICATIONS

This application is the National Stage of International Application No. PCT/US14/12306 filed on Jan. 21, 2014 which claimed priority from provisional application No. 61/754,831 filed on Jan. 21, 2013.

STATEMENT REGARDING FEDERALLY SPONSORED RESEARCH

The research leading to the present invention was supported, in part, by National Institutes of Health grant P01 AT002647 to XM Li.

FIELD OF THE INVENTION

The present invention relates to formulations and methods for the modulation of airway contraction.

BACKGROUND OF THE INVENTION

Asthma, a growing health concern worldwide, particularly in industrialized countries, is a complex disease associated with an elevation of IgE production, abnormally high levels of Th2 cytokines, and airway inflammation. The immediate allergic asthmatic response is the release of histamine and leukotrienes from IgE-activated mast cells that leads to bronchoconstriction and airway hyperreactivity (AHR). Increased airway smooth muscle (ASM) contraction and reduced ASM relaxation in chronic asthma contributes to the excessive airway narrowing and AHR characteristic of asthmatic attacks.

Despite a better understanding of the pathophysiology of asthma, there are still considerable gaps in knowledge as well as a need for new classes of drugs. Current standard asthma management is primarily directed towards suppressing airway inflammation with inhaled corticosteroids (ICSs) and relieving bronchoconstriction with bronchodilators. This standard therapy controls symptoms in most, but not all asthmatic patients while on treatment. Severe asthma is difficult to control. ICSs are generally safe, however, their prolonged use, especially at high doses has been accompanied by concern about both systemic and local side effects. These include osteoporosis, hypothalamic-pituitary-adrenal axis suppression, immune suppression resulting in increased susceptibility to infections such as esophageal candidiasis and frequent upper respiratory tract infections in children, development of cataracts in elderly patients, mood changes, and pharyngitis. Long-term treatment with β2-adrenoceptor (β2-AR) agonists that directly relax ASM contraction, can result in bronchodilator resistance, cardiovascular diseases and arrhythmias. Therefore, development of new alternative or complementary therapies for this disease is becoming increasingly important.

In recent years, interest and use of complementary and alternative medicine (CAM) has been increasing. Traditional Chinese medicine (TCM) has a long history of human use in China and other Asian countries for treating and preventing diseases including asthma, and is part of accepted medical practice in these countries. TCM is also beginning to play a role in the US health care system. There is also increasing scientific understanding of the mechanisms of actions of certain TCMs for allergy and asthma. Kao et al. (2001) showed that the TCM formula xiao-qing-long-tang (XQLT) inhibited bronchoconstriction and airway eosinophil infiltration in ovalbumin-sensitized guinea pigs, and suppressed airway smooth muscle contraction (Kao et al., 2001).

ASHMI™ (Anti-asthma Herbal Medicine Intervention), an aqueous extract of *Ganoderma lucidum* (Fr.) P. Karst. (Ling Zhi), *Sophora flavescens* Aiton (Ku Shen) and *Glycyrrhiza uralensis* Fisch. ex DC (Gan Cao), has been shown to prevent allergic asthma airway hyperreactivity in mice and inhibit acetylcholine (ACh) induced airway smooth muscle (ASM) contraction in tracheal rings from allergic asthmatic mice.

We previously demonstrated that ASHMI™, an aqueous (aq.) extract of *G. lucidum*, *S. flavescens* and *G. uralensis*, eliminated both the immediate airway response and late-phase AHR, and significantly reduced pulmonary inflammation and airway remodeling in a murine allergic asthma model (Busse et al., 2010; Li et al., 2000; Zhang et al., 2010). In a clinical trial, ASHMI™ treatment reduced the use of β2-AR agonists, while significantly improving objective lung function and reducing symptom scores of asthmatics to a similar extent as conventional treatment, and showed a high safety profile (Kelly-Pieper K et al., 2009; Wen et al., 2005). We further found that, in addition to its anti-inflammatory effect, ASHMI™ inhibited ex vivo acetylcholine-induced ASM contractility in tracheal rings of allergic asthmatic mice without activating β2-ARs (Zhang et al., 2010). However, the individual constituent ingredients and compounds responsible for inhibiting ASM contraction have not been identified.

There is therefore a need in the medical arts for an identification and refinement of the bioactive constituents of the ASTHMI™ formula to reduce airway smooth muscle contractility.

SUMMARY OF THE INVENTION

In an embodiment of the present invention the herb *S. Flavescens* is used to reduce activity in contractile tissue, particularly airway smooth muscle.

In an embodiment, the invention comprises aqueous extracts the herb *S. Flavescens* and methods of use thereof to reduce activity in contractile tissue, particularly airway smooth muscle.

In an embodiment the invention comprises, a flavinoid-rich fraction of an extraction of *S. Flavescens* and methods of use thereof to reduce activity in contractile tissue, particularly airway smooth muscle.

In an embodiment the invention comprises, the compounds trifolirhizin and 3',7-dihydroxy-4'-methoxy-isoflavone, either alone or in combination, and methods of use thereof to reduce activity in contractile tissue, particularly airway smooth muscle.

In an embodiment the invention comprises, the compounds Matrine, Oxymatrine and Sophocarpine either alone or in combination, and methods of use thereof to reduce activity in contractile tissue, particularly airway smooth muscle.

In an embodiment the invention comprises an alkaloid rich fraction of an extract of *S. Flavescens* and methods of use thereof to reduce activity in contractile tissue, particularly airway smooth muscle.

In an embodiment the invention comprises a nutritional supplement comprising *S. Flavescens* or extracts thereof.

In an embodiment the invention comprises methods for isolating the bioactive constituents of *S. Flavescens* that have an effect on airway smooth muscle contractility.

BRIEF DESCRIPTION OF THE DRAWINGS

FIGS. 1A-1B. *S. flavescens* inhibits acetylcholine-induced ASM contraction. (A). Effect of ASHMI™ and three individual herb extracts (in concentrations equivalent to that in ASHMI™) on acetylcholine (ACh)-induced contraction of ASM in tracheal rings from sensitized/challenged BALB/c mice. Acetylcholine contractions are expressed as a percent of 60 mM KCl contractions and the graph shows mean±SEM. (n=3 tracheal ring per treatment) (***, p<0.001 significantly different from the control group) The concentrations of ASHMI, *S. flavescens, G. lucidum*, and *G. uralensis* were 100, 45, 35, and 20 μg/ml respectively. (B). Representative myography tracings of control (PBS) (upper tracing) and *S. flavescens*-treated (lower tracing) tracheal rings from sensitized/challenged BALB/c mice.

FIG. 2. Fractionation method of aq. *S. flavescens* extract. MC: Methylene Chloride. MC-F1~5: sub-fractions of methylene chloride extract of aq. *S. flavescens*. Two individual compounds were isolated and named as MC-F1-8S and MC-F1-11S.

FIG. 3. MC extract inhibition of acetylcholine-induced ASM contraction. 30 min pretreatment with 6.0 μg/ml of MC extract was followed by contractile challenges with acetylcholine (ACh) (10-8 M to 10-4 M) in sensitized/challenged mouse tracheal rings. Acetylcholine contractions are expressed as a percent of 60 mM KCl contractions and the graph shows mean±SEM. (n=3 tracheal rings per group) (***, p≤0.001, significantly different from control group).

FIGS. 4A-4C. MC-F1 sub-fraction inhibition of acetylcholine-induced ASM contraction. (A). Acetylcholine (ACh)-stimulated mouse tracheal rings were pre-treated with either MC-F1, 2, 3, 4, or 5 at a concentration of 6.0 μg/ml for 30 min and then stimulated with acetylcholine. Acetylcholine contractions are expressed as a percent of 60 mM KCl contractions. (B). Acetylcholine-stimulated mouse tracheal rings pre-treated with MC-F1 at 0.06, 0.6, and 6.0 μg/ml. Graph shows mean±SEM. (n=3 tracheal rings per group), (, p≤0.01; *, p≤0.001 significantly different from control group). (C). Representative myography tracing of control (PBS) (upper tracing) or MC-F1 (6.0 μg/ml) treated (lower tracing) tracheal rings demonstrating the marked attenuation of acetylcholine-induced contractions in rings pre-treated with MC-F1.

FIGS. 5A-5C. Chemical structures of 3',7-dihydroxy-4'-methoxy-isoflavone and trifolirhizin. (A). Structures of 3',7-dihydroxy-4'-methoxy-isoflavone and trifolirhizin. (B). UV spectrum and TIC data of 3',7-dihydroxy-4'-methoxy-isoflavone and trifolirhizin. (C). MS chromatogram of 3',7-dihydroxy-4'-methoxy-isoflavone and trifolirhizin.

FIGS. 6A-6D. Effects of compounds isolated from MC-F1 on ASM contraction. (A). The effect of 3',7-dihydroxy-4'-methoxy-isoflavone on acetylcholine (ACh)-stimulated ASM contraction. (B). The effect of trifolirhizin on acetylcholine-stimulated ASM contraction. (C). β2-AR antagonist ICI 118,551 (150 μM) did not block the trifolirhizin blockade of acetylcholine-induced contractions. (D) Pretreatment with dexamethasone (10 μM) did not affect acetylcholine-induced contractions. Acetylcholine contractions are expressed as a percent of 60 mM KCl contractions and graph shows mean±SEM. (n=3 tracheal rings per group), significantly different from control group (, p≤0.01; *, p≤0.001 compared to control).

FIGS. 7A-7C. Relaxation effects of trifolirhizin or the β2-AR agonist fenoterol on acetylcholine pre-contracted ASM. (A). The relaxation effect of trifolirhizin on acetylcholine-stimulated tracheal rings with or without ICI 118, 551 (ICI). (B). The relaxation effect of the β2-AR agonist fenoterol on acetylcholine-contracted tracheal rings with or without ICI 118,551; Relaxation is expressed as the percent of residual contractile tone remaining at 15 min after trifolirhizin or fenoterol addition. (C). Representative myography tracings of relaxation experiment using fenoterol (upper tracing), PBS control (middle tracing) or trifolirhizin- (lower tracing) treated sensitized mouse tracheal rings (***, p≤0.001 compared to PBS control). Note the magnitude of total relaxation achieved with trifolirhizin compared to the β2-AR agonist fenoterol.

FIG. 8. Effect ASHMI or component herbs on Ach-induced contraction in tracheal rings from OVA allergic and challenged mice. Rings were pretreated with either 100 μg/ml ASHMI or extracts of *G. lucidum,* 35 μg/ml; *S. flavescens,* 45 μg/ml or *G. uralensis,* 20 μg/ml. Contraction was normalized as percent contraction to 60 mM KCL. Data shown as Mean±SD. of 3-7 tracheal rings from separate mice., P, 0.01 ASHMI vs None; *, P<0.001 ASHMI vs None; ##, P<0.01 SF vs None; ###, P<0.001 SF vs None.

FIG. 9. Effect of solvent fractions of *S. flavescens* on Ach-induced contractility in tracheal rings from OVA-allergic and challenged mice. Rings were pretreated with/without ASHMI (200 μg/ml) or solvent fractions (1-7 at the equivalent of 200 μg/ml ASHMI) for 30 mins. Ring contractility to 10-4 M Ach was normalized to contraction to 60 mM KCL. Data are shown as Mean±SD of 3-7 tracheal rings from separate mice. *, P, 0.001 vs None FIG. 10. Effect of solvent fractions of ASHMI on Ach-induced contractility in tracheal rings from OVA-allergic and challenged mice. Rings were pretreated with/without ASHMI (200 μg/ml) or solvent fractions (1-7 at the equivalent of 200 μg/ml ASHMI) for 30 mins. Ring contractility to 10-4 M Ach was normalized to contraction to 60 mM KCL. Data are shown as Mean±SD of 3-7 tracheal rings from separate mice. *, P, 0.001 vs None; ###, P<0.001 ASHMI vs AS1; ##, P<0.01 AS3 vs AS1

FIG. 11. Structures of Matrine (CAS-number 519-02-8), Sophocarpine (CAS number: 6483-15-4) and Oxymatrine (CAS number: 16837-52-8).

FIG. 12. Representative real time tracing of murine tracheal ring contractions. Rings were first stimulated with 60 mM KCL to assess contractile potential. Compounds (Matrine (40 μM), Oxymatrine (37 μM), sophocarpine (40 μM) or PSS (vehicle) were added 30 minutes prior to stimulation with 10-4 M Ach. Ring viability was tested 90 minutes after Ach washout.

FIG. 13. Effect of Matrine, Sophocarpine and Oxymatrine on tracheal ring responses to 10-4M Ach. Tracheal rings from OVA-allergic and challenged mice were pretreated with either Matrine (40 μM), Sophocarpine (40 μM) or Oxymatrine (37 μM) for 30 mins. Contraction was normalized to percent of contraction to 60 mM KCL. Data are shown as Mean±SD. N=3 rings from separate mice. ***, P, 0.001 vs None; ###, P<0.001 vs Oxymatrine.

FIG. 14: Tracheal rings were washed with PSS buffer 3 times and allowed to rest at 1.00 mN for 30 min after each stimulation. The individual compounds as indicated in this figure were dissolved in DMSO and then re-suspended in PBS (DMSO <0.1%). Each drug was added to the chamber at the concentrations indicated and the pre-incubation time was 30 min. Tracheal rings were then contracted with incremental doses of acetylcholine (from 10-8 M to 10-4 M). PBS (vehicle) treatment was used as control.

Figure 15:
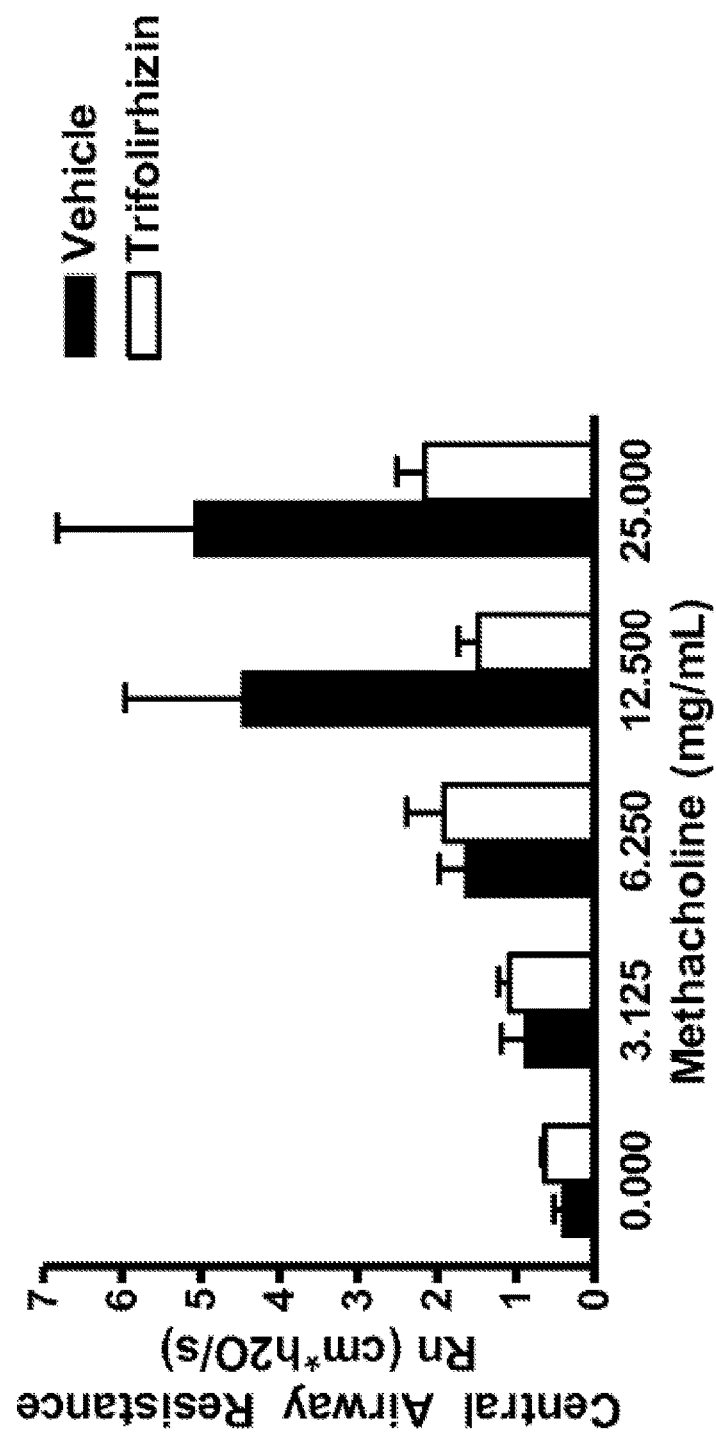

FIG. 15: Airway resistance in male A/J 20 g mice pre-treated with nebulization of vehicle (25 ul 0.3% DMSO) or trifolirhizin (25 ul of 60 ug/ml) 15 minutes before nebulized methacholine as measured by the forced oscillation technique (Flexivent, Scireq). N=3. Nebulized trifolirhizin significantly attenuated increased airway resistance in response to methacholine.

FIG. 16. Table 1. 1H and 13C NMR spectra data of trifolirhizin.

FIG. 17. Table 2. 1H NMR spectra data of 3',7-dihydroxy-4'-methoxy-isoflavone.

FIG. 18. Table 3-1 Fractions generated by Liquid-Liquid Extraction of ASHMI or its component herbs. Solvents used were Dichloromethane, Ethyl Acetate and Methane

DETAILED DESCRIPTION OF THE INVENTION

Dried root of *Sophora flavescens* (Fabaceae), known in Chinese as Ku-Shen, is widely used in traditional Chinese Medicine as a "cooling" drug for the treatment of gastrointestinal hemorrhage, skin diseases, and pyretic stranguria. The herb is an antipyretic, anthelminitic and diuretic agent. Phytochemical studies have revealed the presence of quinolizidine alkaloids and prenylated flavonoids, both of which show a wide spectrum of pharmacological activities.

The present invention provides a *S. Flavescens* extract that is effective in reducing airway smooth muscle (hereinafter "ASM") contraction. In an embodiment the extract may comprise an aqueous extract of S. *Flavescens*. The extract may further comprise flavinoid enhanced fractions of S. *Flavescens*. The extract may further comprise the compound trifolirhizin. In an embodiment of the invention the compound trifolirhizin may be derived from *S. Flavescens* other natural sources or produced synthetically. In an embodiment the invention may comprise the compound 3',7-dihydroxy-4'-methoxy-isoflavone, derived from *S. Flavescens*, or other natural sources or produced synthetically.

In another embodiment, the extract may comprise an alkaloid extraction of *S. Flavescens*. The alkaloid extraction may further comprise the compounds Matrine, Oxymatrine and Sophocarpine. In an embodiment of the invention, the compounds Matrine, Oxymatrine and Sophocarpine may be derived from natural sources such as *S. Flavescens* or produced synthetically.

In an embodiment, a method for reducing the contractility of mammalian airway smooth muscle is described. The method comprises the steps of administering an effective amount of an *S. Flavescens* extract to a mammal.

In another embodiment, the invention is a method for modulating airway contractility by administering to a subject, in need thereof, any of the following compounds, either alone or in combination, along with an acceptable carrier or excipient: trifolirhizin, 3',7-dihydroxy-4'-methoxy-isoflavone, matrine, oxymatrine and sophocarpine Extracts of *S. flavescens* may be obtained through any appropriate methods known to those skilled in the art. For example, aq. extracts of ASHMI™ and the individual herbal medicines, *G. lucidum, S. flavescens* and *G. uralensis* were provided by Sino-lion (Zhong Shi) Pharmaceutical Company (Weifang, China). Each raw herb was soaked in water for 30 min, and then boiled for 2 hr. The decoction was then concentrated under reduced pressure (P=0.08 Mpa), and thermal spray dried. Based on the ratio of individual raw herbs *G. Lucidum, S. flavescens* and *G. uralensis* in the ASHMI™ formula (62.5%, 28.1% and 9% respectively), and the yield of extracts of *G. lucidum, S. flavescens*, and *G. uralenisis* (6%, 20% and 17% respectively), ASHMI™ used in this study was a combination of the 3 herbal extracts in a ratio of 35%, 45%, 20% of *G. lucidum, S. flavescens* and *G. uralenisis* respectively. HPLC grade methylene chloride, ethyl acetate, acetonitrile with 0.1% formic acid, potassium chloride, and aluminum hydroxide (Alum, Imject®) were purchased from Fisher Scientific (Pittsburgh, Pa.). Albumin (OVA, Grade VI), Acetylcholine chloride (ACh, 99%), ICI 118,551 hydrochloride (>98% TLC), dexamethasone, and fenoterol hydrobromide were purchased from Sigma Aldrich (St Louis, Mo.).

The present invention also provides a dietary supplement comprising any of the *S. Flavescens* extracts of the invention. The *S. Flavescens* extracts or individual compounds extracted therefrom may be formulated into dietary supplements, including capsules, tablets, powders, solutions, gels, suspensions, creams, pastes, gels, suppositories, transdermal patches, and the like. These dietary supplements in, for instance, powder or solution form, may be added to nutraceuticals, foods and/or beverages to form functional nutraceutical, food, and/or beverage products. The dietary supplements may be formulated as powders, for example, for mixing with consumable liquids such as milk, juice, water or consumable gels or syrups for mixing into other dietary liquids or foods. The dietary supplements of this invention may be formulated with other foods or liquids to provide pre-measured supplemental foods, such as single serving bars. Typical food products that may incorporate the *S. Flavescens* extract of the present invention include dairy foods such as yogurt, cereals, breads, snack food products, fruit juices and other soft drinks Flavorings, binders, protein, complex carbohydrates, vitamins, minerals and the like may be added as needed. Preferably, the *S. Flavescens* extract is formulated for oral administration.

The present invention also provides a dietary supplement comprising of the *S. Flavescens* extracts described herein. The dietary supplement when administered to a mammal, including humans, may reduce Airway Smooth Muscle contractility, and therefore be a useful treatment for asthma. A successful course of treating, for instance, individuals with asthma, is characterized, inter alia, by causing the Airway Smooth Muscle of those individuals to relax and/or reduce contractility.

The dietary supplements of the present invention are intended for daily administration or as needed. The magnitude of a prophylactic or therapeutic dose of the dietary supplement in asthmatic individuals will vary with the severity of the condition being treated and the route of administration. The dose, and perhaps the dose frequency, will also vary according to the age, body weight, and response of the individual.

The dietary supplements of the present invention may be formulated in a conventional manner (i.e. by dry mixing, dry or wet granulation, direct compression), in admixture with pharmaceutically acceptable carriers, excipients, vitamins, minerals and/or other nutrients. Representative carriers and excipients include, but are not limited to, starches, sugars, microcrystalline cellulose, diluents, granulating agents, lubricants, binders, disintegrating agents, and the like, in the case of oral solid preparations (such as powders, capsules, and tablets).

Any suitable route of administration may be employed to administer the dietary supplements of the invention to an individual. Suitable routes include, for example, oral, rectal, parenteral, intravenous, topical, transdermal, subcutaneous, and intramuscular. Although any suitable route of administration may be employed for providing the patient with an effective amount of the extract according to the methods of the present invention, oral administration is preferred, including solid dosage forms such as tablets, capsules, or powders. It is also preferred that the extract is formulated for use in functional nutraceutical, food, or beverage products.

An embodiment of the invention is a method for treating disorders of bronchoconstriction or airway contractility, as in, for example, asthma, in a subject in need thereof which comprises administering to the subject a therapeutically effective amount of any of the extracts or compounds, or compositions described herein.

Also included in the invention is the use of any of the extracts described herein for the preparation of a medicament for treating disorders of bronchoconstriction or airway contractility, as in, for example, asthma in a subject in need thereof. The term "treating" as used herein refers to a method for improving, halting, retarding or palliating disorders of bronchoconstriction or airway contractility, as in, for example, asthma in the subject in need thereof. All such methods of treatment are intended to be within the scope of the present invention.

In accordance with the methods of the present invention, the individual components of the compositions described herein can also be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal (preferably, a mammal; most preferably, a human) who has been the object of treatment, observation, or experiment.

The term "therapeutically effective amount" as used herein, means that amount of active compound, or extract, or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare the compositions of this invention, one or more extracts of *S. Flavescens*, or compounds purified therefrom, as the active ingredient(s), is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a composition of the present invention in liquid dosage form for oral, topical, inhalation/insufflation and parenteral administration, any of the usual pharmaceutical media or excipients may be employed. Thus, for liquid dosage forms, such as suspensions (i.e., colloids, emulsions and dispersions) and solutions, suitable carriers and additives include but are not limited to pharmaceutically acceptable wetting agents, dispersants, flocculation agents, thickeners, pH control agents (i.e., buffers), osmotic agents, coloring agents, flavors, fragrances, preservatives (i.e., to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents, and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid compositions such as tablets, the principal active ingredient is mixed with a pharmaceutical carrier, e.g., conventional tabletting ingredients such as diluents, binders, adhesives, disintegrants, lubricants, antiadherents, and glidants. Suitable diluents include, but are not limited to, starch (i.e., corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e., AVICEL™ microcrystalline cellulose available from FMC Corp.), dicalcium phosphate, calcium sulfate dihydrate, calcium lactate trihydrate, and the like. Suitable binders and adhesives include, but are not limited to *acacia* gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e., alginic acid and salts thereof, magnesium aluminum silicate, hydroxyethylcellulose (i.e. TYLOSE™ available from Hoechst Celanese), polyethylene glycol, polysaccharide acids, bentonites, polyvinylpyrrolidone, polymethacrylates and pregelatinized starch), and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e., corn starch, etc.), gums (i.e., agar, guar, locust bean, karaya, pectin, and tragacanth gum), cross-linked polyvinylpyrrolidone, and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate, and the like. Suitable gildants include, but are not limited to, talc, cornstarch, silica (i.e., CAB-O-SIL™ silica available from Cabot, SYLOID™ silica available from W. R. Grace/Davison, and AEROSIL™ silica available from Degussa), and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation, and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate, cellulose acetate phthalate, polyvinyl acetate phthalate, hydroxypropyl methylcellulose phthalate, hydroxypropyl methylcellulose acetate succinate, methacrylate and ethylacrylate copolymers, and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e., beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e., propylene alginate, sodium alginate, and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e., carboxypolymethylene), and polyethylene glycol; clays such as bentonite, hectorite, attapulgite or sepiolite; and other pharmaceutically acceptable suspending agents such as lecithin, gelatin, or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235, and combinations thereof. Suitable deflocculating or dispersing agent include pharmaceutical grade lecithins. Suitable flocculating agent include but are not limited to simple neutral electrolytes (i.e., sodium chloride, potassium, chloride, and the like), highly charged insoluble polymers and polyelectrolyte species, water soluble divalent or trivalent ions (i.e., calcium salts, alums or sulfates, citrates and phosphates (which can be used jointly in formulations as pH buffers and flocculating agents). Suitable preservatives include but are not limited to parabens (i.e., methyl, ethyl, n-propyl and n-butyl), sorbic acid, thimerosal, quaternary ammonium salts, benzyl alcohol, benzoic acid, chlorhexidine gluconate, phenylethanol, and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers, and the like. Conversely, polar liquids such as water, alcohols, polyols and glycols are best used with suspending agents such as higher HLB surfactants, clays silicates, gums, water soluble cellulosics, water soluble polymers, and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, extracts and/or compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Extracts and/or compounds of the present invention can also be administered in a form suitable for intranasal or inhalation therapy. For such therapy, extracts and/or compounds of the present invention are conveniently delivered in the form of a solution or suspension from a pump spray container that is squeezed or pumped or as an aerosol spray from a pressurized container or a nebulizer (such as, a metered dose inhaler, a dry powder inhaler or other conventional or non-conventional modes or devices for inhalation delivery) using a suitable propellant (such as, dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (such as, those made from gelatin) for use in an inhaler or insufflator may be formulated containing a powder mix of a compound of the invention and a suitable powder base such as lactose or starch.

Extracts and/or compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines, and the like.

Extracts and/or compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxyethylaspartamidephenol, and polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates, and cross-linked or amphipathic block copolymers of hydrogels and blends thereof.

The therapeutically effective amount of extracts and/or compounds or composition thereof may be from about 0.001 mg/kg/dose to about 300 mg/kg/dose. Preferably, the therapeutically effective amount may be from about 0.001 mg/kg/dose to about 100 mg/kg/dose. More preferably, the therapeutically effective amount may be from about 0.001 mg/kg/dose to about 50 mg/kg/dose. Most preferably, the therapeutically effective amount may be from about 0.001 mg/kg/dose to about 30 mg/kg/dose. Therefore, the therapeutically effective amount of the active ingredient contained per dosage unit (e.g., tablet, capsule, powder, injection, suppository, teaspoonful, and the like) as described herein will be in the range of from about 1 mg/day to about 21,000 mg/day for a subject, for example, having an average weight of 70 kg. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. Advantageously, compounds of the present invention may be administered in a single daily dose or the total daily dosage may be administered in divided doses of two, three or four times daily.

Preparation of Flavonoid Rich Fraction from S. flavescens by Methylene Chloride Extraction Enrichment for flavinoids may be accomplished through any appropriate methods known to those skilled in the art. For example, we first used methylene chloride (MC) extraction to generate less-polar compounds (FIG. 2). 101.27 g of dried S. flavescens aqueous extract was dissolved in 4.0 L of distilled water and extracted with 3.0 L of methylene chloride for 24 hr in a liquid-liquid extractor (Sigma-Aldrich) at 100° C. using a 2 L heating mantle (EM2000/CX1, Barnstead International, Dubuque, Iowa). The methylene chloride extract of S. flavescens (MC-extract) was dried with a rotary evaporator (Rotavapor R-210, BÜCHI, Switzerland) and lyophilized (LYPH•LOCK 6 freeze dry system, LABCONCO, Kansas City, Mo.).

Preparation of MC Sub-Fractions and Individual Compounds by Preparative HPLC

A 100 mg/ml MC-extract solution was prepared by dissolving MC extract powder into a mixture of water and acetonitrile (v:v=1:1) containing 0.1% formic acid and loaded into a preparative HPLC system. Separation was performed on a C18 reverse phase preparative column (XBridge™ Prep C18 5 μm OBD™, 19×150 mm, Waters, Milford, Mass.) with distilled water as mobile phase A and acetonitrile containing 0.1% formic acid as mobile phase B at a constant flow rate of 20 ml/min and detected under photodiode array (PDA) detector at wavelength 254 nm. The initial gradient was 30% B for 20 min; increased to 50% in 4 min; increased to 100% B in 2 min; maintained at 100% for another 2 min. Five sub-fractions were collected according to a time based collection method (MC-F1~5).

Further separation of MC-F1 sub-fractions was performed using preparative HPLC. 19 subfractions were collected, and each fraction was analyzed using analytical HPLC. Those fractions containing individual peaks were dried under vacuum, and their structures determined using NMR and LC-MS. The fractions containing multiple-peaks were saved for further separation.

Isolation and Identification of 3',7-Dihydroxy-4'-Methoxy-Isoflavone and Trifolirhizin from MC-F1:

Isolation of individual compounds contained in S. Flavescens may be accomplished through any method known to those having skill in the art. For example, the MC-F1 fraction was further fractionated by preparative HPLC and 19 subfractions were collected. Based on analytical HPLC chromatograms subfractions 8 and 11 each contained a single peak, designated MC-F1-8S and MC-F1-11S (purity >90%). The remaining fractions containing either mixtures (not pure) or flow through solvent were combined for further investigation. The structures of these compounds (FIG. 5A) were identified as 3',7-dihydroxy-4'-methoxy-isoflavone (8S) and trifolirhizin (11S) using liquid chromatography mass spectrometry (LC-MS), 1H and 13C NMR spectroscopy. LC-MS was first used to analyze these two subfractions. The UV spectrum data and total ion chromatography (TIC) are shown in FIG. 5B. Mass spectral data of MC-F1-8S showed a strong [M+H]+ ion at m/z 285. Data for MC-F1-11S indicated that m/z 285, 447, and 464 corresponded to [M-O-Glc]+, [M+H]+, and [M+NH4]+, respectively (FIG. 5C). The molecular weights (MW) of MC-F1-8S and MC-F1-11S were then determined to be 284 and 446 respectively. Both the 1H NMR and 13C NMR data of trifolirhizin are collected and shown in Table 1 (FIG. 16) and agree with previously reported data (Abdel-Kader, 2010; Hyun et al., 2008; Zhang et al., 2007; Zhou et al., 2009). Based on the HPLC, LC-MS data, the 1H NMR data (Table 2 (FIG. 17)) of MC-F1-8S and the previous publication (Hyun et al., 2008), its structure was identified as 3',7-dihydroxy-4'-methoxy-isoflavone.

LC-MS and NMR Method

Mass spectra data were collected on a micromass LCT premier TOF mass spectrometer (Waters Corporation, Milford, Mass.) coupled with a Waters Alliance 2695 HPLC system in a positive electrospray mode (ESI+). 1H and 13C NMR spectra were obtained on a JOEL instrument (at 300 MHz for 1H NMR and 75 MHz for 13C NMR) using DMSO-d6 as the solvent.

HPLC Quantification

Quantification of the biologically active compounds present in S. flavescens was performed by HPLC. The analyses were carried out with a Waters Alliance 2695 separation module (Waters) equipped with PDA detector. The separation was performed on a Zorbax-C18 (150×4.6 mm) column with mobile phase A (0.1% formic acid) and B (CH3CN) at a flow rate of 1.0 ml/min. The linear gradient from 2% to 46% B over 75 min was used for separation. Samples were dissolved in mobile phase mixture (v:v=1:1). UV wavelength was monitored from 210 nm to 400 nm. Five different concentrations of standard compound (5, 8, 10, 12, and 15 μg/ml) were prepared and analyzed with HPLC and the Empower software (Waters). The calibration curve was generated by using peak area obtained at 254 nm of standard at different concentrations. The R2 was 0.9995.

Characterization of the S. Flavescens Extract and Flavinoid Enhanced S. Flavescens Extract S. flavescens Inhibited Acetylcholine-Induced ASM Contraction in Tracheal Rings from Asthmatic Mice To determine which herbal constituents in ASHMI™ have a direct inhibitory effect on ASM contraction, an asthmatic mouse model was induced by ovalbumin (OVA) sensitization and challenge as described previously (Zhang et al., 2010). Tracheal rings from asthmatic mice were treated with an aq. extract of ASHMI™ (100 μg/ml), or individual herb aq. extracts, G. lucidum (35 μg/ml), S. flavescens (45 μg/ml) and G. uralenisis (20 μg/ml), for 30 min prior to ex vivo acetylcholine provocation. The ASHMI™ concentration was based on our previous publication (Zhang et al., 2010). Concentrations of individual herb extracts were equivalent to their individual concentrations in ASHMI™. ASHMI™ treatment significantly reduced acetylcholine-induced ASM contraction in tracheal rings over a range of 10-6 M-10-4 M acetylcholine (FIG. 1A, p<0.001 vs control phosphate buffered saline (PBS)-treated tracheal rings). These results are consistent with our previous publication (Zhang et al., 2010). S. flavescens extracts at a concentration equivalent to that in ASHMI™ inhibited acetylcholine-induced ASM contraction to the same degree as ASHMI™ (p<0.001, FIGS. 1A, and B, myography tracing). G. lucidum and G. uralensis at their ASHMI™ equivalent concentrations did not inhibit contraction (FIG. 1A).

Figure 2:
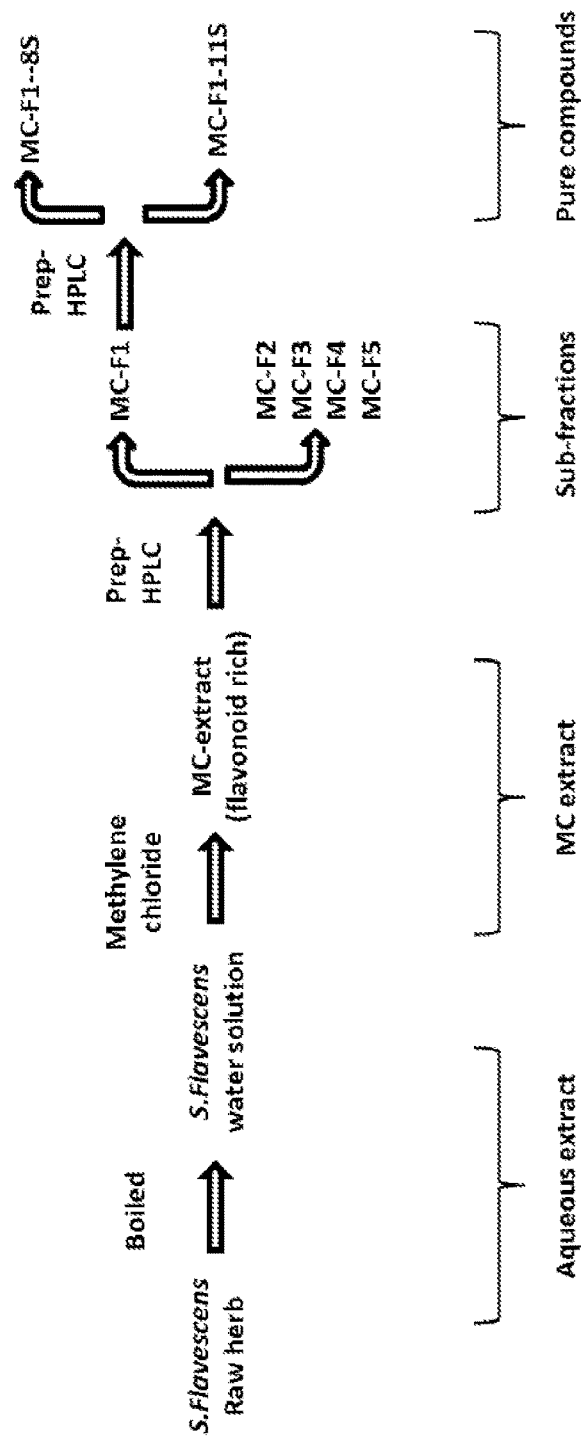
Figure 3:
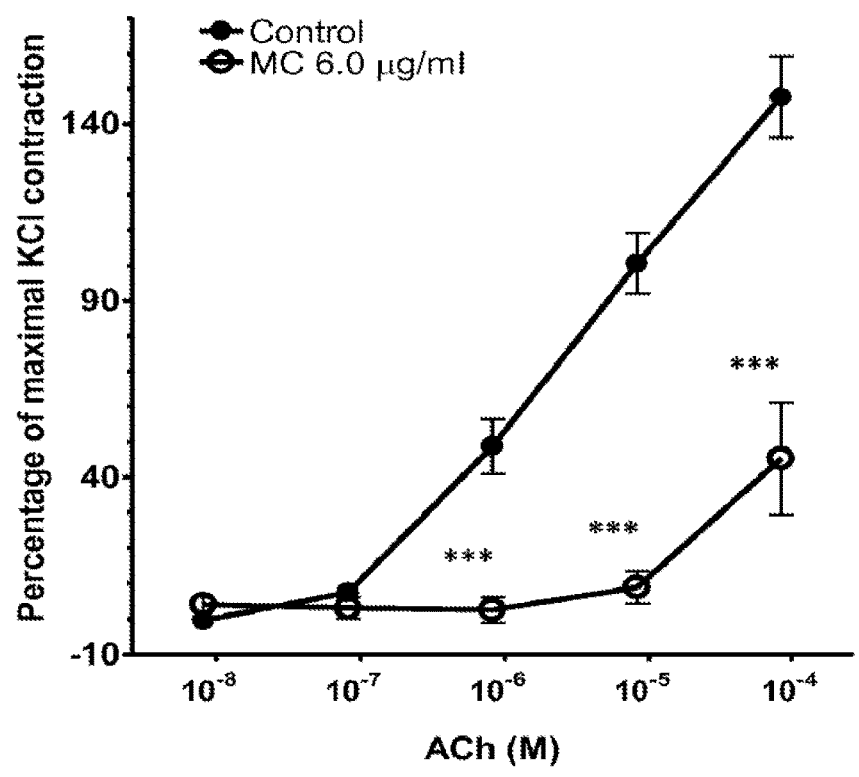
Figures 4A, 4B:
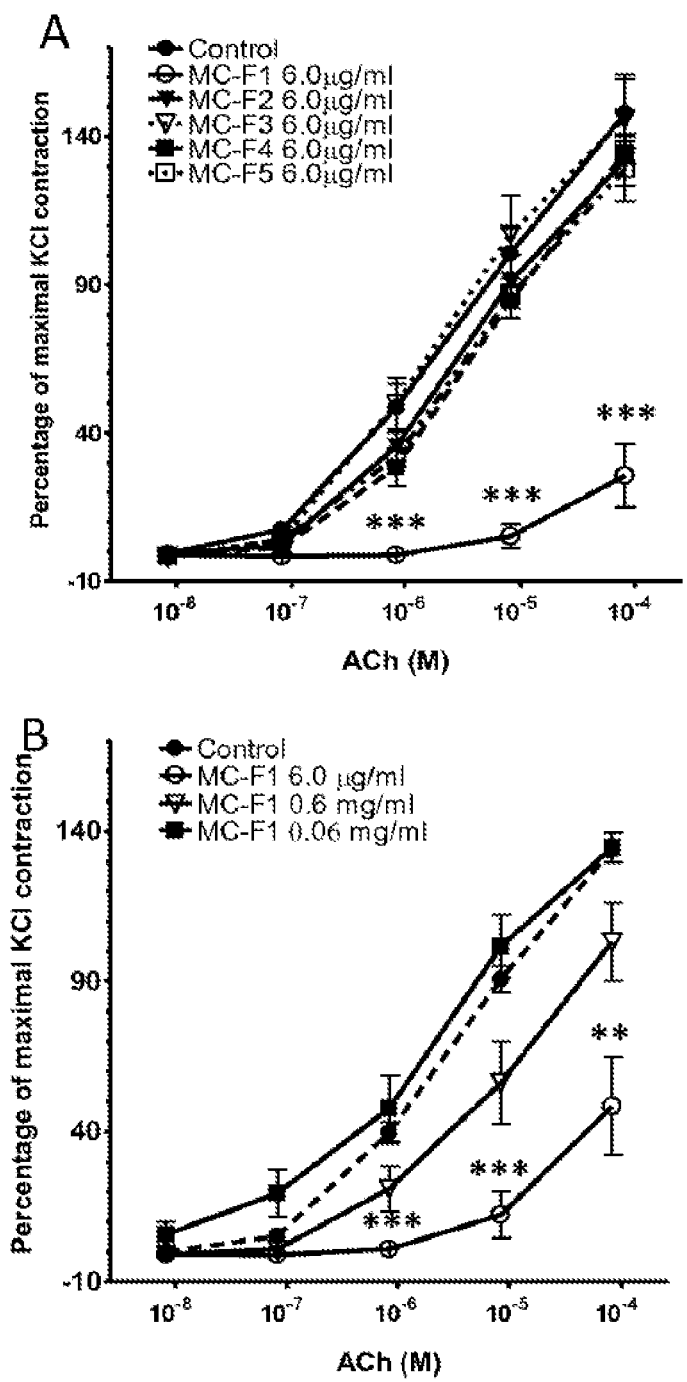
Figure 4C:
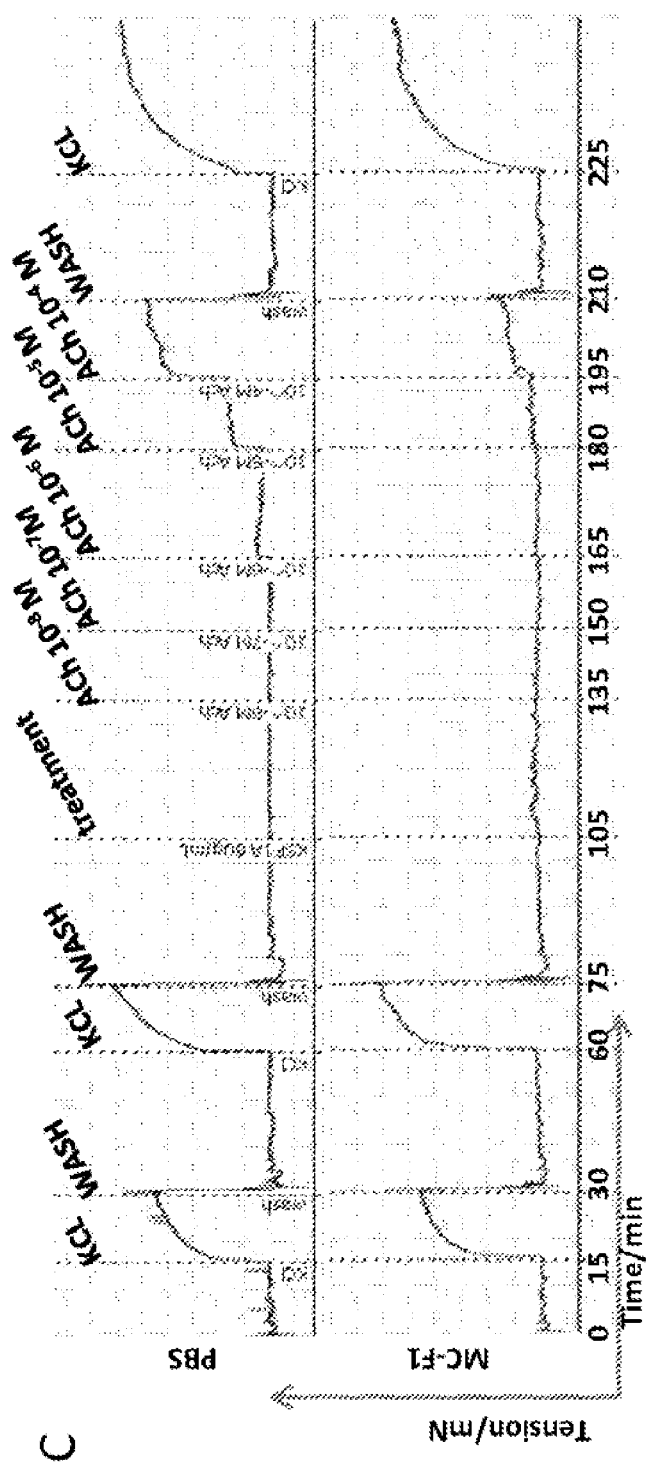

Identification of the S. flavescens Flavonoid Fraction and Subfraction that Inhibit Acetylcholine-Induced ASM Contraction We first generated a methylene chloride (MC) extract from an aq. extract of S. flavescens to obtain a flavonoid rich extract (designated MC extract, FIG. 2). Preliminary work, reported in an abstract (Liang B et al., 2010), showed that 6.0 μg/ml MC extract (equivalent to 84.5m/ml of aq S. flavescens extract) inhibited ASM contraction to 10-4 M acetylcholine. In the current study, we determined the effect of the MC extract (6.0 μg/ml) on ASM contraction in tracheal rings from asthmatic mice to incremental concentrations of acetylcholine ranging from 10-8 to 10-4 M. The MC extract significantly inhibited acetylcholine-induced contraction (FIG. 3, p<0.001 vs. control). We next generated 5 sub-fractions (MC-F1, 2, 3, 4 and 5) using preparative HPLC and tested each at 6.0 μg/ml. Only MC-F1 significantly suppressed ASM contraction to acetylcholine (FIG. 4A, p<0.001 vs. control). Other fractions did not have a significant effect (FIG. 4A vs. control), even at 2-5 times higher concentrations (data not shown). The inhibition of ASM contraction by MC-F1 was concentration-dependent (FIG. 4B) and non-toxic as contractile responses to KCl were present after buffer washings (FIG. 4C). These findings show that sub-fraction MC-F1 contains the active flavonoid(s) and thus it was subjected to further fractionation and identification of single compounds.

Isolation and Identification of 3',7-Dihydroxy-4'-Methoxy-Isoflavone and Trifolirhizin from MC-F1

The MC-F1 fraction was further fractionated by preparative HPLC and 19 subfractions were collected. Based on analytical HPLC chromatograms subfractions 8 and 11 each contained a single peak, designated MC-F1-8S and MC-F1-11S (purity >90%). The remaining fractions containing either mixtures (not pure) or flow through solvent were combined for further investigation. The structures of these compounds (FIG. 5A) were identified as 3',7-dihydroxy-4'-methoxy-isoflavone (8S) and trifolirhizin (11S) using liquid chromatography mass spectrometry (LC-MS), 1H and 13C NMR spectroscopy. LC-MS was first used to analyze these two subfractions. The UV spectrum data and total ion chromatography (TIC) are shown in FIG. 5B. Mass spectral data of MC-F1-8S showed a strong [M+H]+ ion at m/z 285. Data for MC-F1-11S indicated that m/z 285, 447, and 464 corresponded to [M-O-Glc]+, [M+H]+, and [M+NH4]+, respectively (FIG. 5C). The molecular weights (MW) of MC-F1-8S and MC-F1-11S were then determined to be 284 and 446 respectively. Both the 1H NMR and 13C NMR data of trifolirhizin are collected and shown in Table 1 (FIG. 16) and agree with previously reported data (Abdel-Kader, 2010; Hyun et al., 2008; Zhang et al., 2007; Zhou et al., 2009). Based on the HPLC, LC-MS data, the 1H NMR data (Table 2 (FIG. 17)) of MC-F1-8S and the previous publication (Hyun et al., 2008), its structure was identified as 3',7-dihydroxy-4'-methoxy-isoflavone.

Trifolirhizin Inhibited ASM Contraction

Figures 6A, 6B, 6C, 6D:
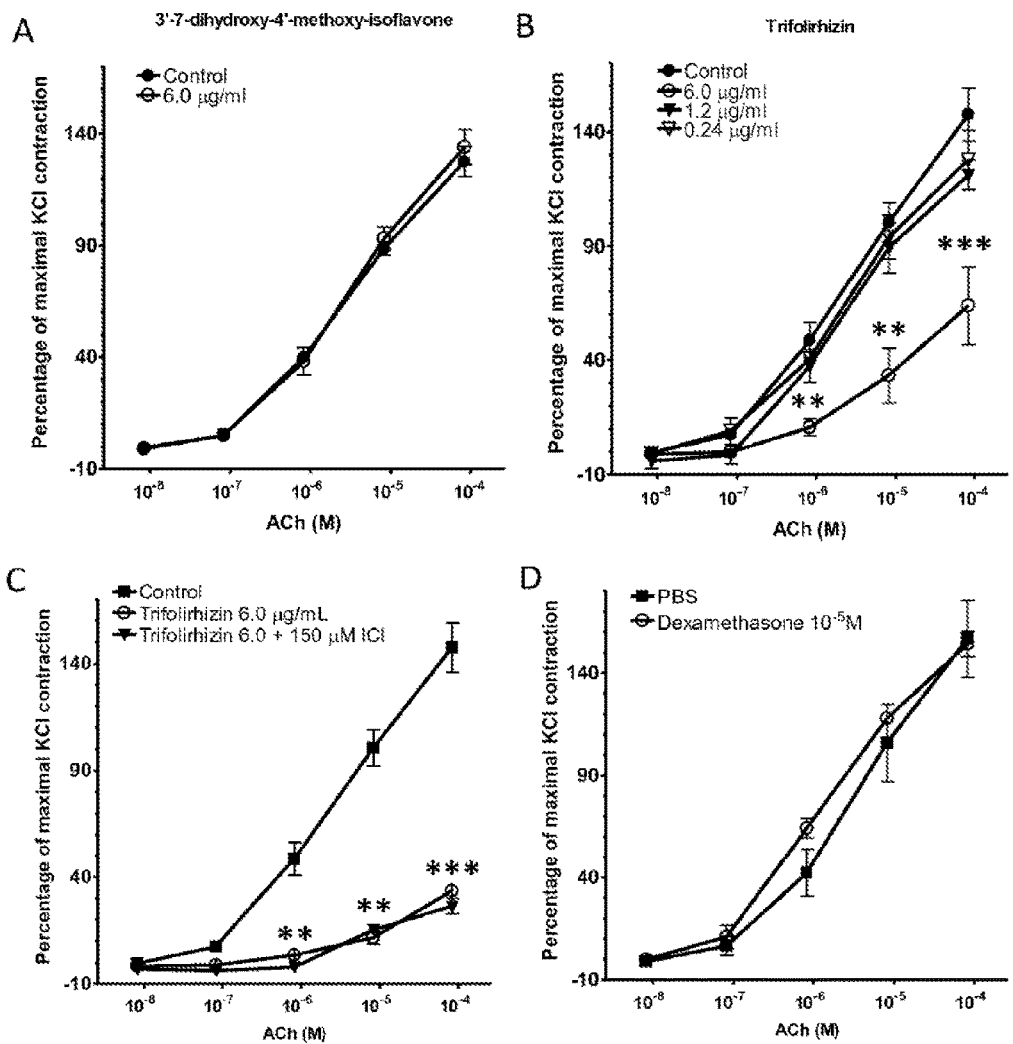

3',7-dihydroxy-4'-methoxy-isoflavone (6.0 μg/ml) had no effect on ASM contraction to acetylcholine (FIG. 6A). Trifolirhizin significantly inhibited acetylcholine-induced contraction at 6.0 μg/ml, but not at lower concentrations (FIG. 6B, p<0.01-0.001). β2-AR agonists are commonly used therapeutics to prevent ASM contraction or facilitate ASM relaxation. To determine whether a mechanism of trifolirhizin's effect on ASM contraction involved β2-ARs, sensitized murine tracheal rings were preincubated with or without trifolirhizin (6.0 μg/ml) and with or without the β2-AR antagonist ICI 118,551 (150 μM) for 30 min before acetylcholine contractions. The β2-AR antagonist had no effect on trifolirhizin's ability to impair an acetylcholine contraction (FIG. 6C). Dexamethasone is commonly used as a treatment for acute asthma. Therefore, we tested the ability of an acute dexamethasone pretreatment to inhibit acetylcholine-induced contractions in sensitized murine tracheal rings. Dexamethasone (10 μM) did not inhibit the acetylcholine-induced ASM contractions (FIG. 6D).

Studies of pharmacological actions of trifolirhizin are limited. It has been shown to inhibit inflammatory responses (Zhou et al., 2009), and melanin synthesis by melanoma cells (Yu et al., 1999). However, it has not previously been evaluated for a potential effect on ASM. Our study is the first demonstration that trifolirhizin inhibits ASM contraction. A previous open label study reported that S. flavescens aq. extract produced remarkable clinical improvement of asthma symptoms, reduction of b2 agonist use, dose of inhaled corticosteroid, and improvement of PEF in refractory asthmatics (Hoang et al., 2007). Hoang et. al. suggested that the two major matrine-type alkaloids, matrine and oxymatrine, may be the primary active components in the herbal mixture responsible for the anti-asthma effect (Hoang et al., 2007). However, S. flavescens contains not only matrine-type alkaloids, it also contains active flavonoids which may contribute other anti-asthmatic effects (Jin et al., 2010).

In another open label study S. flavescens aq. extract was given by inhalation. Wheezing and chest pain diminished, and in some cases disappeared in 10 minutes, and this effect lasted for up to 36 hours (Zhang et al., 2010). Our current study is the first to identify the S. flavescens flavonoid trifolirhizin as an active compound that contributes to S. flavescens inhibition of ASM contraction. Mechanisms of ASM modulation are complex, but mainly involve G protein-coupled receptors (GPCRs) controlling intracellular calcium and the responsiveness of the actin myosin complex. Gs-coupled receptors, including β2-ARs and prostaglandin E2 receptors, primarily mediate relaxation as a consequence of cAMP signaling. Gq and Gi-coupled receptors include muscarinic M3, histamine H1 and leukotriene CysLT1 mediate contraction (Zhang et al., 2007). Activation of Gq-coupled receptors results in activation of phospholipase C, increased intracellular Ca+2 and ASM contraction. Activation of receptors coupled to Gi (such as adenosine A1/A3, and muscarinic M2) leads to inhibition of adenylyl cyclase, and activation of phospholipase C. Aberrant GPCR signaling in ASM may contribute to elevated ASM tone in asthma. Our previous study showed that ASHMI inhibition of ASM contraction is β2-AR independent (Zhang et al., 2010) and that was confirmed for trifolirhizin in the present study where pretreatment with the β2-AR antagonist, ICI 118,551 did not block the effect of trifolirhizin's pretreatment on impairment of acetylcholine in sensitized murine tracheal rings (FIG. 6C).

Trifolirhizin Relaxed the Pre-Contracted Tracheal Rings

Figures 7A, 7B, 7C:
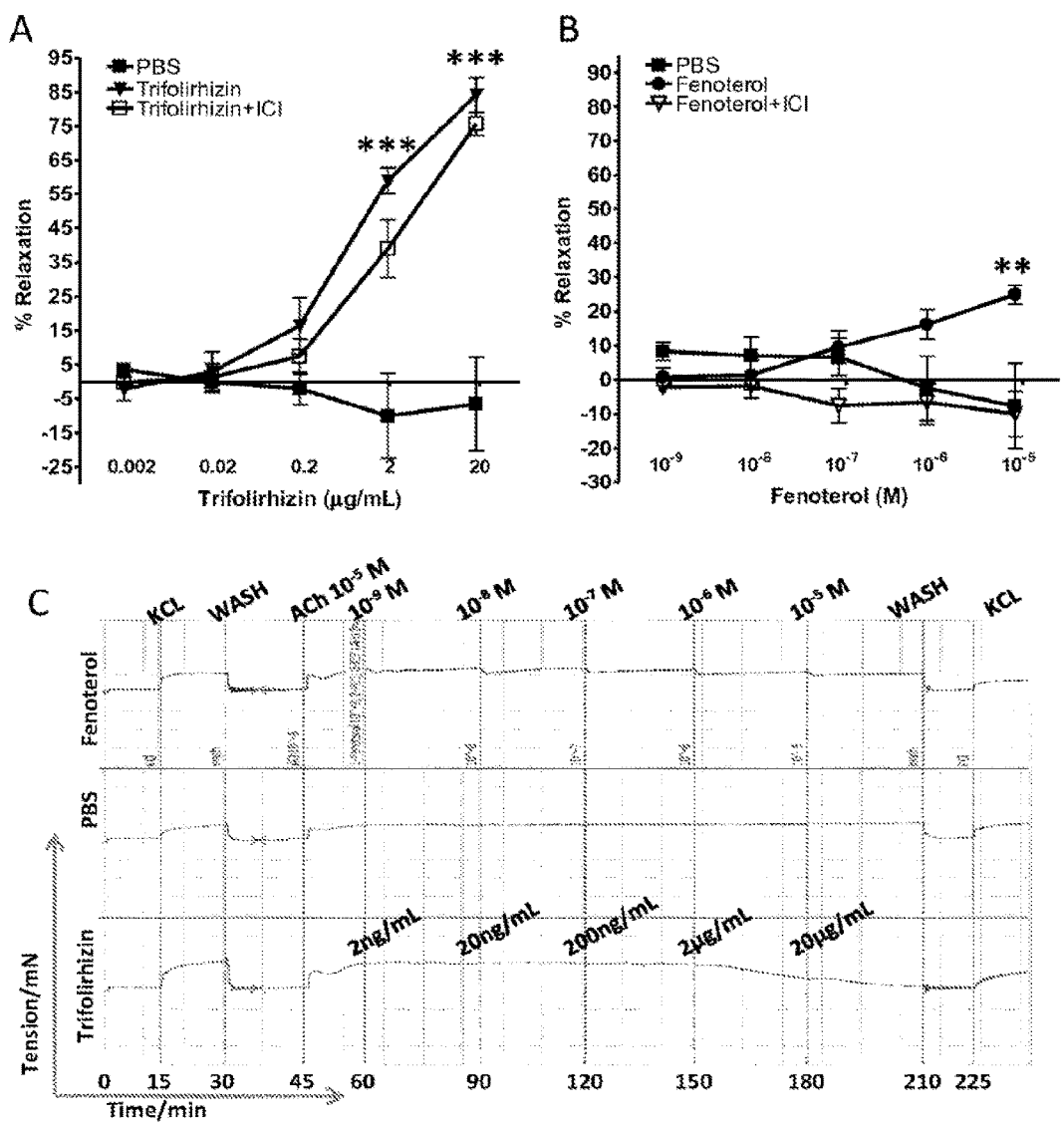
Figure 8:
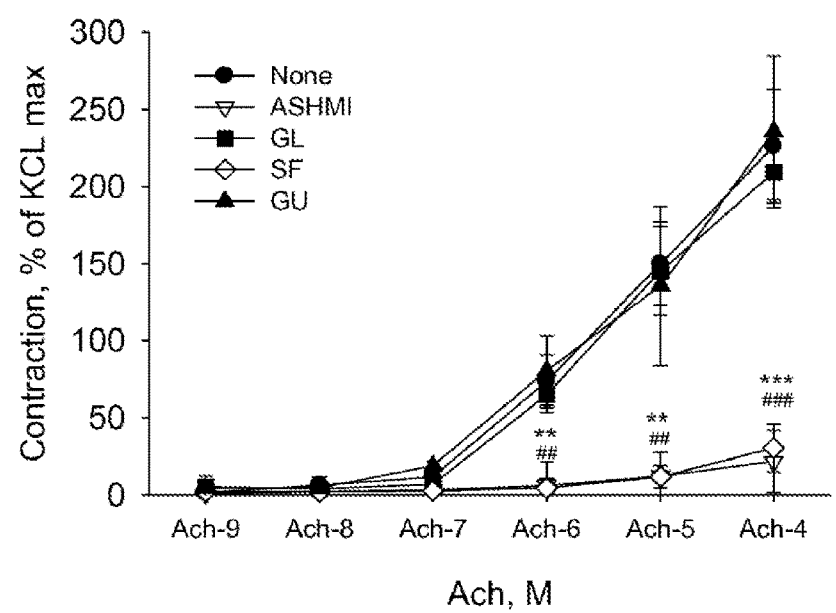

The primary therapy for acute constriction of airway smooth muscle is β2-AR agonists which are inhaled for the acute relaxation of hyperresponsive airway smooth muscle. We performed studies with trifolirhizin to determine whether it could relax pre-contracted airway smooth muscle and how the magnitude of relaxation compared to a classic β2-AR agonist fenoterol. In order to investigate the relaxation effect of trifolirhizin on ASM, we tested this isolated compound on acetylcholine pre-contracted sensitized murine tracheal rings. Trifolirhizin relaxed the pre-contracted tracheal rings stimulated by 10-5 M acetylcholine in a dose-dependent manner. The maximal relaxation was 85% of the initial contractile tone at a trifolirhzin concentration of 20 μg/ml (FIG. 7A). In parallel studies the β2-AR agonist fenoterol only achieved 25% relaxation even at the highest concentration tested (10-5 M). We also observed that fenoterol relaxed the contraction of tracheal rings immediately after the addition but slowly lost its effect with increasing time of incubation which is consistent with desensitization of the β2-AR, a mechanism thought in part responsible for β2-agonists' limitations in the treatment of acute allergic asthma. Co-incubation of the β2-AR antagonist, ICI 118,551 with trifolirhizin was without effect on the inhibition capability of trifolirhizin (FIG. 7A), while ICI 118,551 completely blocked the effect of fenoterol (FIG. 7B).

Quantification

The amount of bioactive flavonoid trifolirhizin present in the S. flavescens was quantified by HPLC. Pure trifolirhizin at five different concentrations 5.0 to 15.0 μg/ml were analyzed on HPLC. The calibration curves were plotted using the peak areas of each condition and the equation of the peak area and the concentration was generated. The trifolirhizin concentration in the aqueous extract of S. flavescens was approximately 6.7 μg/100 mg. Previous in vitro use of trifolirhizin involved concentrations ranging from 10-20 μM to 100-200 μM in the cultures of mouse J774A.1 macrophages (McGraw et al., 2003), or 50 μM in the cultures of melanoma B16 cells. The trifolirhizin concentration used in our ex vivo study was 6.0 μg/ml (13.4 μM), which is in the lower range of concentrations shown to be active in other systems. Although effective concentrations for ASM were comparable to those previously reported, they reflect higher concentrations than would occur in ASHMI™. Whether this reflects the presence of other ASM-relaxant compounds in ASHMI™, or potentiation of trifolirhizin by other ASHMI™ components, is yet unknown.

Characterization of the Alkaloid S. Flavescens Extracts

ASHMI-Mediated Suppression of Tracheal Contractility is Reproduced by S. flavescens but not G. lucidum or G. uralensis Murine tracheal rings from OVA-allergic mice were pretreated for 30 minutes with either 100 ug/ml of ASHMI, 35 ug/ml of G. lucidum or 20 ug/ml of G. uralensis. Tracheal ring contraction to Ach was markedly suppressed by ASHMI as expected ($P<0.01$ to $P<0.001$ vs None). Of the three herbs tested, only S. flavescens reduced Ach-induced contractility. At 45 μg/ml, S. flavescens was able to reproduce the degree of suppression observed in rings treated with ASHMI. ($P<0.01$ to $P<0.001$ vs None). Extracts of G. lucidum or G. uralensis did not alter tracheal ring contractility to the doses of Ach tested.

Figure 9:
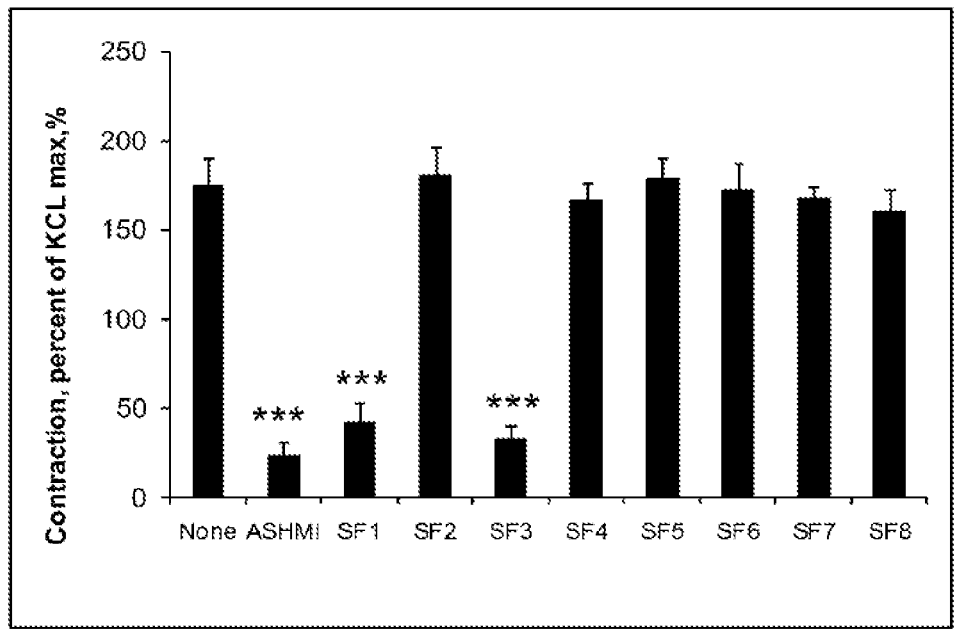

Dichloromethane Soluble Fractions of S. flavescens Potently Inhibit Tracheal Ring Contractility to Ach We tested solvent fractions of S. flavescens (SF1-7) for their potential to inhibit tracheal contraction to Ach. As shown in FIG. 9 Fractions 1 (basic dichloromethane soluble) and 3 (acidic dichloromethane soluble) demonstrated potent suppression of contraction to Ach. Fractions 2 and 4-7 had no impact on Ach-induced contraction. All fractions were tested at the equivalence of 200 μg/ml ASHMI.

Figure 10:
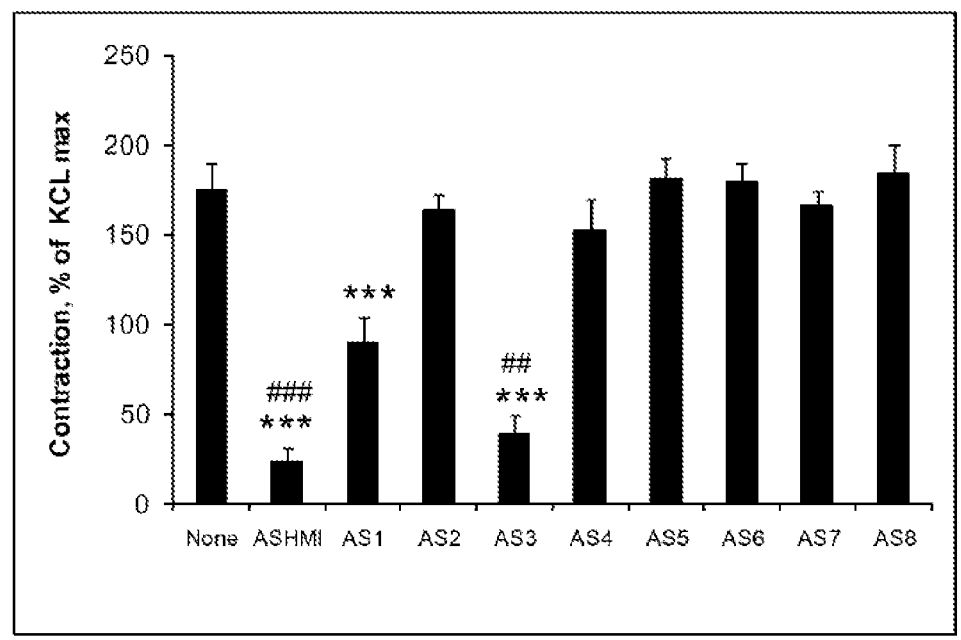

The Basic Dichloromethane Soluble Fraction (F3) of Whole ASHMI Potently Suppresses Ach-Stimulated Contraction To verify if indeed the Fraction 1 and 3 (dichloromethane soluble) components were functional in whole ASHMI fractions we also evaluated fractions of ASHMI generated using similar methods used to fractionate S. flavescens. We found that ASHMI fraction 3 (AS3) as observed for SF fraction 3 dramatically inhibited tracheal contractility (FIG. 10). AS1 also inhibited contraction (P<0.001 vs None) but to a significantly lesser extent that fraction 3 (P<0.001 AS 1 vs AS 3).

Matrine Type Alkaloids Inhibit Tracheal Ring Contraction to Ach

Figure 11:
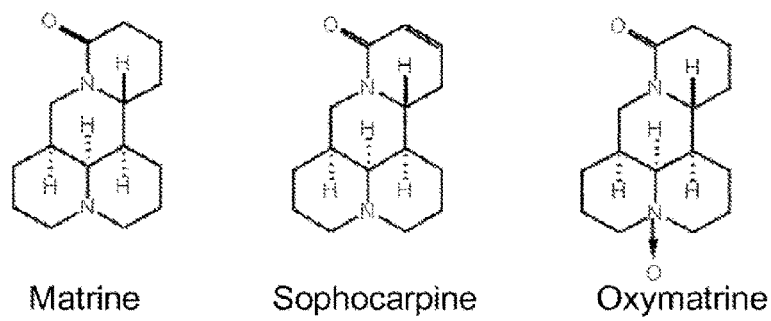
Figure 12:
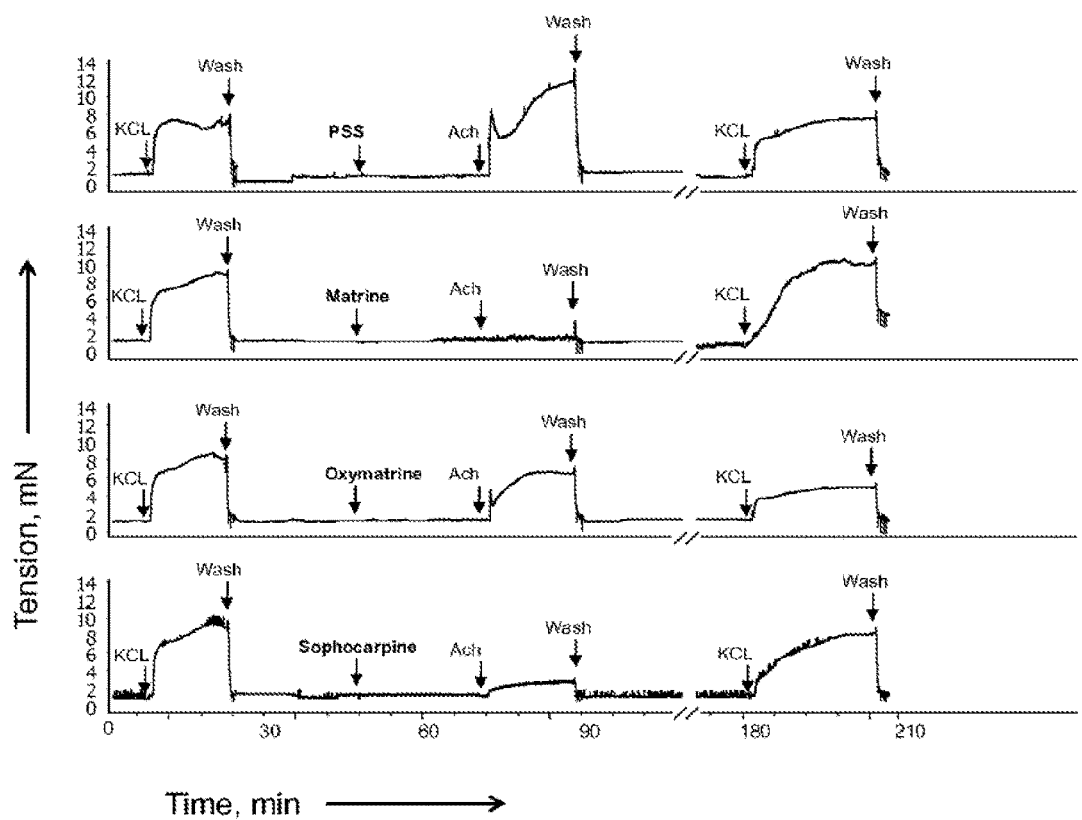
Figure 13:
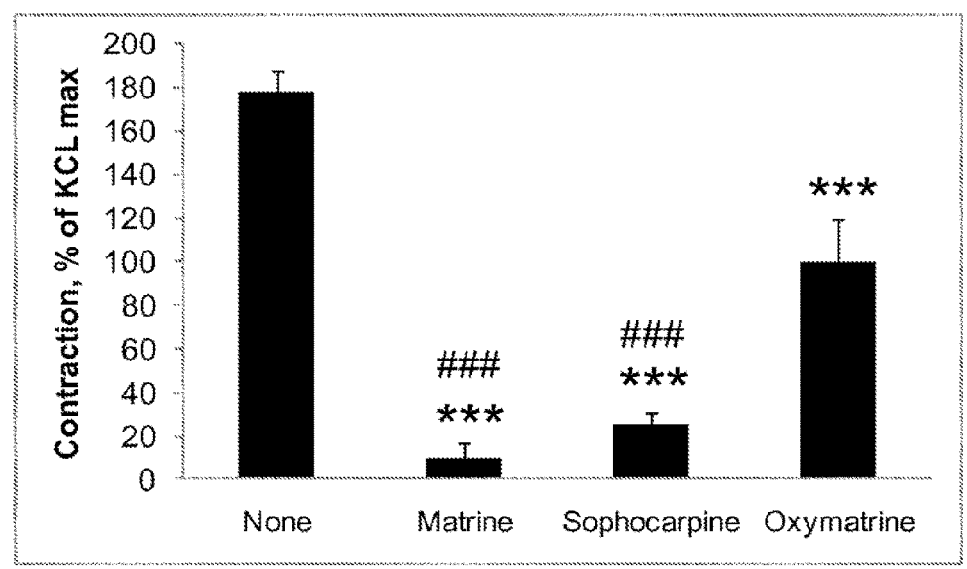

Having observed that Fraction 3 of *S. flavescens* was a potent inhibitor of Ach-stimulated tracheal contraction we tested major compounds present in this fraction in myography experiments. According to investigations using mass spectrometric techniques, the major compounds identified in SF Fraction 3 were the matrine type alkaloids-Matrine, Oxymatrine and Sophocarpine. The structures of these compounds are shown in FIG. 11. When tested at 10 µg/ml we found that all three compounds inhibited Ach-induced contraction in when tested in ex vivo myography experiments. As shown in real time tracings (FIG. 12) and numerical data from multiple experiments (FIG. 13), Matrine was the most potent followed by sophocarpine. Oxymatrine was the weakest inhibitor of contraction when compared to Matrine and Sophocarpine. As was observed in the case ASHMI treatment, all three compounds did not exhibit toxicity to tracheal tissue as rings were responsive to KCL when tested 90 minutes after washout Data from multiple experiments are shown in FIG. 13. As suggested by real-time tracings shown in FIG. 12, all three compounds inhibited Ach-stimulated contraction (P<0.001 vs None for all). However, Matrine and Sophocarpine were found to be more effective than Oxymatrine (P<0.001 vs Oxymatrine for both)

Results described in this study shed light on the identity of compounds participating in the direct effects of ASHMI on airway contractility. It appears that anti-contractile responses of ASHMI are restricted to those contained in *S. flavescens*. Furthermore, only the dichloromethane soluble fractions of both ASHMI and *S. flavescens* demonstrated inhibitory activity. The basic Dichloromethane soluble fraction (Fraction 3) was of special interest as Fraction 3 of both ASHMI and *S. flavescens* were the effective at inhibiting contraction. Communications with Dr. LaVerne Brown and Dr. Nan Yang have indicated that Fraction 3 of ASHMI is mostly comprised of compounds from *S. flavescens* supporting the observation that AS3 and SF3 were similar in their ability to suppress tracheal contractility to Ach. Interestingly while SF1 showed very potent inhibitory effects, the corresponding fraction of ASHMI (AS1) was not as effective. This may likely be attributed to the fact that *S. flavescens* compounds of fraction 1 display altered extractability or function when fractionated as a part of whole ASHMI. SF1 compounds are being actively investigated by my lab colleague Banghao Liang.

Further focusing on SF3, its major compounds Matrine, Sophocarpine and Oxymatrine were tested by tracheal ring myography and results indicate that these matrine type alkaloids have considerable inhibitory activity on tracheal contractility. This is the first known demonstration of anti-contractile properties of these compounds in the airway. Experiments suggest that, similar to ASHMI, suppressive effects of these alkaloids are also inhibited by Indomethacin.

Matrine, Oxymatrine and Sophocarpine are well known quinolizidine alkaloids found in many *Sophora* species 3-5. Matrine and Oxymatrine in particular have been investigated in human and animal studies in China. Most studies have focused on the anti-cancer and anti-viral properties of these compounds. Mechanistic studies are largely restricted to anti-cancer research and include regulation of cancer-relevant proteins such as ERK, Bcl-2 family of proteins, telomerase and mitochondrial caspases. Of note, a few publications have noted that matrine and oxymatrine protect from cardiac arrhythmia in rat models 0.13 The mechanism of protection was suggested to be related to beneficial modulation of $Ca^{2+}$ transience in myocytes. More recent publications suggest that Matrine has anti-inflammatory properties by virtue of inhibition of NFkB signaling. It is yet undetermined if mechanisms proposed in the above mentioned studies have relevance to observation in our experiments. The doses of Matrine or Oxymatrine used for experiments in cancer cell lines are often 25-50 fold higher than the dose of 10 µg/ml used in our study and the effects are usually observed over treatment of several hours if not days. Studies related to anti-inflammatory properties also use similarly high doses. An added difficulty of understanding the research literature about matrine compounds is the lack of availability of English translations of many publications. Currently, there is little research on matrine alkaloids outside of China.

Example Method #1 Fractionation, Isolation and Purification of Compounds Fractionation A dried aqueous extract of SF (200 g) was dissolved in water (4 L) and loaded on macroporous resin column (Amberlite* XAD-7 HP, Acros Organics, New Jersey, USA), and sequentially eluted with distilled water, 20% ethanol, 50% ethanol, and 95% ethanol, sequentially. The 4 fractions were concentrated under reduced pressure, to yield SFF1, SFF2, SFF3 and SFF4.

Isolation and Purification

GU-F2 (20 g) was subjected on silica gel column chromatography, eluted with dichloromethane-ethyl acetate-methanol (5:4:0), dichloromethane-ethyl acetate-methanol (5:4:0.5), dichloromethane-ethyl acetate-methanol (5:4:1), dichloromethane-ethyl acetate-methanol (5:4:2), dichloromethane-ethyl acetate-methanol (5:4:4), with 0.5% ammonium hydroxide (30%), sequentially. Elute were collected each 300 ml, on the basis of TLC profiles, fractions were combined with one purified compound or 2-3 major compounds. SFF2-15 and SFF2-17 were labeled as PC-2A and PC2B, sequentially. PC2 contains single peak.

Example Method #2 Myograph for Measurement of ASM Contractility Ex Vivo

Animal Sensitization and Challenge

Balb/c mice were sensitized by intraperitoneal (i.p.) injection of 200 µg OVA plus 2 mg of aluminum hydroxide (alum) in 400 µl of PBS on days 0 and 7. Mice were challenged intratracheally (i.t.) with 100 µg of OVA in 50 µl of PBS weekly for 2 weeks (days 14 and 21). Mice were challenged i.t. once daily with 100 µg of OVA (50 µl) on 2 consecutive days (days 28 and 29) 48 hr before sacrifice and tissue harvesting.

Measurement of ASM Contractility Ex Vivo

Figure 14:
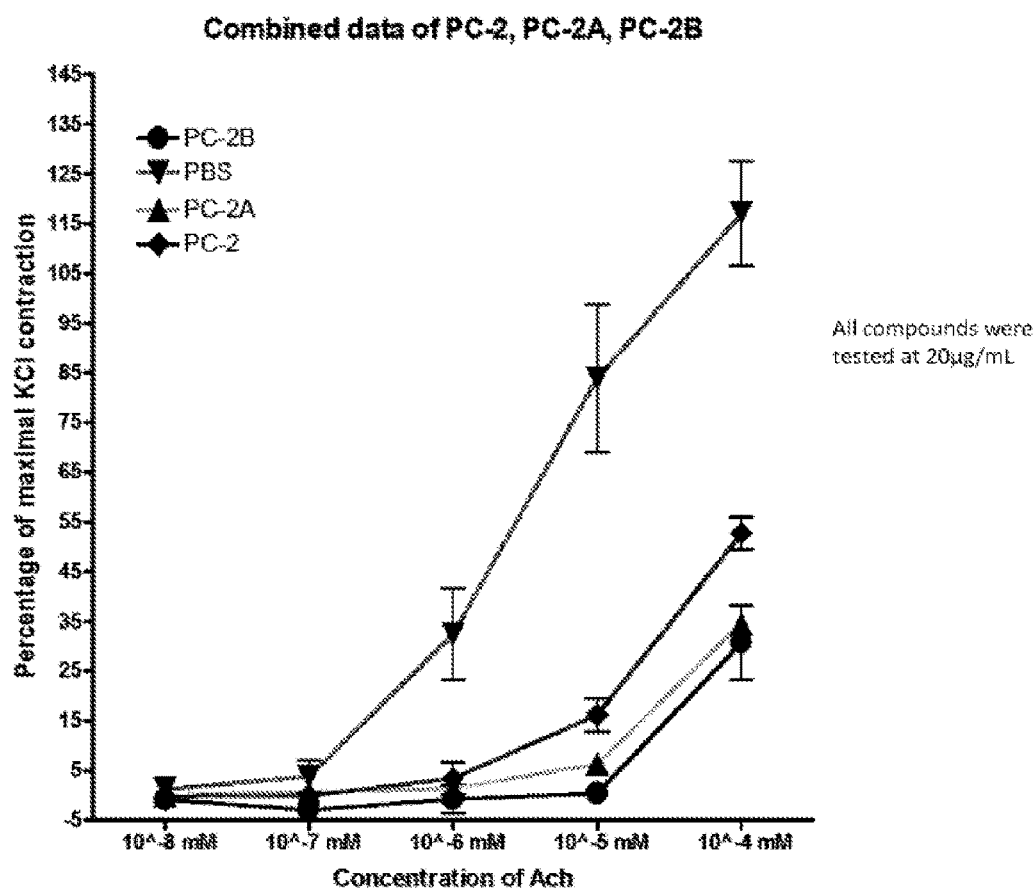

Forty-eight hrs after the last i.t. OVA challenge, mice were sacrificed and tracheas were excised and cut into 3 tracheal rings as previously described. Each tracheal ring was attached to a pair of mounting pins in the organ chamber of a Myograph System Model 610M system (AD Instruments, Denver, Colo.) and bathed in a chamber containing physiological salt solution (PSS (In g/L—NaCl: 6.95, KCl: 0.35, MgSO4.7H2O: 0.28, KH2PO4: 0.1561, CaCl2.2H2O: 0.36, NaHCO3: 2.1, EDTA: 0.01, Glucose: 1.09, pH=7.4). All chambers were maintained at 37° C. and were continuously bubbled with 100% O2. The change of tracheal ring tension was recorded by Power Lab Chart recording software (AD Instruments). After incubation at 37° C. for 15 min at baseline tension, passive tension applied to the tracheal ring was adjusted to 1.00 mN. Following stabilization of passive tension, tracheal rings were contracted using 60 mM KCl twice, to assess ASM contractility. Tracheal rings were washed with PSS buffer 3 times and allowed to rest at 1.00 mN for 30 min after each stimulation. The individual compounds as indicated in FIG. 14 were dissolved in DMSO and then re-suspended in PBS (DMSO <0.1%). Each drug was added to the chamber at the concentrations indicated and the pre-incubation time was 30 min. Tracheal rings were then contracted with incremental doses of acetylcholine (from $10^{-8}$ M to $10^{-4}$ M). PBS (vehicle) treatment was used as control.

REFERENCES

Abdel-Kader, M. S., 2010. Preliminary pharmacological study of the pterocarpans macckian and trifolirhizin isolated from the roots of Ononis vaginalis. Pak. J. Pharm. Sci. 23, 182-187

Akinbami, L. J., Moorman, J. E., Garbe, P. L., Sondik, E. J., 2009. Status of childhood asthma in the United States, 1980-2007. Pediatrics 123 Suppl 3, S131-S145

Barrios, R. J., Kheradmand, F., Batts, L., Corry, D. B., 2006. Asthma: pathology and pathophysiology. Arch. Pathol. Lab Med. 130, 447-451

Bensky D, Clayey S, Stoger E, 2004. Chinese Herbal Medicine: Material and Meidica. 3rd, 1-1311

Bensky D and Gamble A, 1993. Chinese Herbal Medicine: Materia Medica. Revised Edition, 1-556

Bhalla, R. K., Taylor, W., Jones, A. S., Roland, N. J., 2008. The inflammation produced by corticosteroid inhalers in the pharynx in asthmatics. Clin Otolaryngol. 33, 581-586

Bielory, L., Russin, J., Zuckerman, G. B., 2004. Clinical efficacy, mechanisms of action, and adverse effects of complementary and alternative medicine therapies for asthma. Allergy Asthma Proc. 25, 283-291

Billington, C. K. and Penn, R. B., 2003. Signaling and regulation of G protein-coupled receptors in airway smooth muscle. Respir. Res. 4, 2-25

Braman, S. S., 2006. The global burden of asthma. Chest 130, 4S-12S

Busse, P. J., Schofield, B., Birmingham, N., Yang, N., Wen, M. C., Zhang, T., Srivastava, K., Li, X. M., 2010. The traditional Chinese herbal formula ASHMI inhibits allergic lung inflammation in antigen-sensitized and antigen-challenged aged mice. Ann. Allergy Asthma Immunol. 104, 236-246

CDC, 2011. National Center for Health Statistics: Asthma. http://www.cdc.gov/nchs/fastats/asthma.htm [Accessed Jan. 18, 2012]

Cordina, M., Fenech, A. G., Vassallo, J., Cacciottolo, J. M., 2009. Anxiety and the management of asthma in an adult outpatient population. Ther. Adv. Respir. Dis. 3, 227-233

Fukushima, C., Matsuse, H., Tomari, S., Obase, Y., Miyazaki, Y., Shimoda, T., Kohno, S., 2003. Oral candidiasis associated with inhaled corticosteroid use: comparison of fluticasone and beclomethasone. Ann. Allergy Asthma Immunol. 90, 646-651

Hall, I. P., 2004. The beta-agonist controversy revisited. Lancet 363, 183-184

Hoang, B. X., Shaw, D. G., Levine, S., Hoang, C., Pham, P., 2007. New approach in asthma treatment using excitatory modulator. Phytother. Res. 21, 554-557

Holgate, S. T., Peters-Golden, M., Panettieri, R. A., Henderson, W. R., Jr., 2003. Roles of cysteinyl leukotrienes in airway inflammation, smooth muscle function, and remodeling. J. Allergy Clin. Immunol. 111, S18-S34

Hyun, S. K., Lee, W. H., Jeong, d. M., Kim, Y., Choi, J. S., 2008 Inhibitory effects of kurarinol, kurardinol, and trifolirhizin from Sophora flavescens on tyrosinase and melanin synthesis. Biol. Pharm. Bull. 31, 154-158

Jin, J. H., Kim, J. S., Kang, S. S., Son, K. H., Chang, H. W., Kim, H. P., 2010. Anti-inflammatory and anti-arthritic activity of total flavonoids of the roots of Sophora flavescens. J Ethnopharmacol. 127, 589-595

Kao, S. T., Lin, C. S., Hsieh, C. C., Hsieh, W. T., Lin, J. G., 2001. Effects of xiao-qing-long-tang (XQLT) on bronchoconstriction and airway eosinophil infiltration in ovalbumin-sensitized guinea pigs: in vivo and in vitro studies. Allergy 56, 1164-1171

Kawai, M., Hirano, T., Higa, S., Arimitsu, J., Maruta, M., Kuwahara, Y., Ohkawara, T., Hagihara, K., Yamadori, T., Shima, Y., Ogata, A., Kawase, I., Tanaka, T., 2007. Flavonoids and related compounds as anti-allergic substances. Allergol. Int. 56, 113-123

Kelly-Pieper K, Patil S P, Busse P, Yang N, Sampson H, Wisnivesky J, Li, X.-M., Kattan M., 2009. Safety and tolerability of an antiasthma herbal formula (ASHMI™) in adult asthmatics: a randomized, double-blinded, placebo-controlled, dose escalation phase I study. J. Altern. Complement Med. 15, 735-743

Lemanske, R. F. J., 1998. A review of the current guidelines for allergic rhinitis and asthma. J. Allergy Clin. Immunol. 101, S392-S396

Li, X. M., 2009. Complementary and alternative medicine in pediatric allergic disorders. Curr. Opin. Allergy Clin Immunol. 9, 161-167

Li, X. M. and Brown, L., 2009. Efficacy and mechanisms of action of traditional Chinese medicines for treating asthma and allergy. J. Allergy Clin. Immunol. 123, 297-306

Li, X. M., Huang, C. K., Zhang, T. F., Teper, A. A., Srivastava, K., Schofield, B. H., Sampson, H. A., 2000. The chinese herbal medicine formula MSSM-002 suppresses allergic airway hyperreactivity and modulates TH1/TH2 responses in a murine model of allergic asthma. J. Allergy Clin. Immunol. 106, 660-668

Liang B, Brown L L, Srivastava K, Birmingham N, Li X, 2010 Inhibitory Effect of Ku-Shen Sub-fractions on Murine Airway Smooth Muscle Contraction. J. Allergy Clin. Immunol. (Abstract). 125, S 200-200

Lipworth, B. J., 1999. Systemic adverse effects of inhaled corticosteroid therapy: A systematic review and meta-analysis. Arch. Intern. Med. 159, 941-955

Liu, G., Dong, J., Wang, H., Hashi, Y., Chen, S., 2011. Characterization of alkaloids in Sophora flavescens Ait. by high-performance liquid chromatography-electrospray ionization tandem mass spectrometry. J Pharm. Biomed. Anal. 54, 1065-1072

McGraw, D. W., Almoosa, K. F., Paul, R. J., Kobilka, B. K., Liggett, S. B., 2003. Antithetic regulation by beta-adrenergic receptors of Gq receptor signaling via phospholipase C underlies the airway beta-agonist paradox. J. Clin. Invest. 112, 619-626

Noonan, M., Leflein, J., Corren, J., Staudinger, H., 2009. Long-term safety of mometasone furoate administered via a dry powder inhaler in children: Results of an open-label study comparing mometasone furoate with beclomethasone dipropionate in children with persistent asthma. BMC. Pediatr. 9, 43-50

Packe, G. E., Robb, O., Robins, S. P., Reid, D. M., Douglas, J. G., 1996. Bone density in asthmatic patients taking inhaled corticosteroids: comparison of budesonide and beclomethasone dipropionate. J R. Coll. Physicians Lond. 30, 128-132

Plusa, T., 2010. [Agonists of beta2 adrenergic receptor in the therapy of obstructive diseases]. Pol. Merkur Lekarski. 28, 8-12

Roland, N. J., Bhalla, R. K., Earis, J., 2004. The local side effects of inhaled corticosteroids: current understanding and review of the literature. Chest. 126, 213-219

Salpeter, S. R., Ormiston, T. M., Salpeter, E. E., 2004. Meta-analysis: respiratory tolerance to regular beta2-agonist use in patients with asthma. Ann. Intern. Med. 140, 802-813

The National Institute of Allergy and Infectious Diseases (NIAID)., 2010. Asthma and Allergic Diseases Cooperative Research Centers (U19). http://grants nih gov/grants/guide/rfa-files/RFA-AI-10-013 html (accessed Sep. 19, 2010)

The State Pharmacopoeia Commission of The People's Republic of China, 2005. Pharmacopoeia of the People's Republic of China. Version 6, 1-791

Toogood, J. H., Crilly, R. G., Jones, G., Nadeau, J., Wells, G. A., 1988. Effect of high-dose inhaled budesonide on calcium and phosphate metabolism and the risk of osteoporosis. Am. Rev. Respir. Dis. 138, 57-61

Wang, J. J., Rochtchina, E., Tan, A. G., Cumming, R. G., Leeder, S. R., Mitchell, P., 2009. Use of inhaled and oral corticosteroids and the long-term risk of cataract. Ophthalmology. 116, 652-657

Wen, M. C., Wei, C. H., Hu, Z. Q., Srivastava, K., Ko, J., Xi, S. T., Mu, D. Z., Du, J. B., Li, G. H., Wallenstein, S., Sampson, H., Kattan, M., Li, X. M., 2005. Efficacy and tolerability of anti-asthma herbal medicine intervention in adult patients with moderate-severe allergic asthma. J. Allergy Clin. Immunol. 116, 517-524

Yu, Q., Wang, P., Liu, L., et al, 1999. Ku-Shen. Chinese edition, 208-213

Zhang, L., Xu, L., Xiao, S. S., Liao, Q. F., Li, Q., Liang, J., Chen, X. H., Bi, K. S., 2007. Characterization of flavonoids in the extract of Sophora flavescens Ait. by high-performance liquid chromatography coupled with diode-array detector and electrospray ionization mass spectrometry. J Pharm. Biomed. Anal. 44, 1019-1028

Zhang, T., Srivastava, K., Wen, M. C., Yang, N., Cao, J., Busse, P., Birmingham, N., Goldfarb, J., Li, X. M., 2010. Pharmacology and immunological actions of a herbal medicine ASHMI on allergic asthma. Phytother. Res. 24, 1047-1055

Zhou, H., Lutterodt, H., Cheng, Z., Yu, L. L., 2009. Anti-Inflammatory and antiproliferative activities of trifolirhizin, a flavonoid from Sophora flavescens roots. J Agric. Food Chem. 57, 4580-4585

Zollner, E. W., 2007. Hypothalamic-pituitary-adrenal axis suppression in asthmatic children on inhaled corticosteroids (Part 2)—the risk as determined by gold standard adrenal function tests: a systematic review. Pediatr. Allergy Immunol. 18, 469-474

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

What is claimed is:

1. A method for treating asthma in a subject in need thereof comprising administering an effective amount of an extract of Sophora flavescens enriched in flavonoids and alkanoids, wherein the extract is obtained by:
    a) extracting Sophora flavescens with water to provide an aqueous extract; and
    b) extracting the aqueous extract of Sophora flavescens with methylene chloride to provide said extract.

2. The method of claim 1, wherein the subject is a human.

3. The method of claim 1, wherein the extract of S. flavescens is enriched in 3',7-dihydroxy-4'-methoxy-isoflavone and trifolirhizin.

4. The method of claim 1, wherein the extract of S. flavescens is enriched in trifolirhizin.

5. The method of claim 1, wherein the extract of S. flavescens is enriched in matrine type alkaloids.

6. The method of claim 1, wherein the extract of S. flavescens is enriched in matrine, oxymatrine and sophocarpine.

7. The method of claim 1, wherein the extract of S. flavescens is enriched in matrine and sophocarpine.

8. The method of claim 1, wherein the extract of S. flavescens is enriched in matrine.

9. A method for treating asthma in a subject in need thereof comprising administering an effective amount of a fraction of Sophora flavescens enriched in flavonoids and alkanoids, wherein the fraction is obtained by:
    a) extracting Sophora flavescens with water to provide an aqueous extract;
    b) extracting the aqueous extract of Sophora flavescens with methylene chloride to provide a methylene chloride extract; and
    c) subjecting the methylene chloride extract to chromatographic fractionation to provide the fraction.

10. The method of claim 9, wherein said chromatographic fractionation is High-Performance Liquid Chromatography (HPLC).

11. The method of claim 9, wherein the extract of S. flavescens is enriched in 3',7-dihydroxy-4'-methoxy-isoflavone and trifolirhizin.

12. The method of claim 9, wherein the extract of S. flavescens is enriched in trifolirhizin.

13. The method of claim 9, wherein the extract of S. flavescens is enriched in matrine type alkaloids.

14. The method of claim 9, wherein the extract of S. flavescens is enriched in matrine, oxymatrine and sophocarpine.

15. The method of claim 9, wherein the extract of S. flavescens is enriched in matrine and sophocarpine.

16. The method of claim 9, wherein the extract of S. flavescens is enriched in matrine.

* * * * *